(12) United States Patent
Belle et al.

(10) Patent No.: US 7,592,350 B2
(45) Date of Patent: Sep. 22, 2009

(54) POLYCYCLIC COMPOUNDS AS POTENT ALPHA2-ADRENOCEPTOR ANTAGONISTS

(75) Inventors: David Din Belle, Espoo (FI); Reija Jokela, Helsinki (FI); Arto Tolvanen, Espoo (FI); Antti Haapalinna, Turku (FI); Arto Karjalainen, Espoo (FI); Jukka Sallinen, Turku (FI); Jari Ratilainen, Kulho (FI)

(73) Assignee: Orion Corporation, Espoo (FI)

( * ) Notice: Subject to any disclaimer, the term of this patent is extended or adjusted under 35 U.S.C. 154(b) by 534 days.

(21) Appl. No.: 10/510,019

(22) PCT Filed: Apr. 3, 2003

(86) PCT No.: PCT/FI03/00255

§ 371 (c)(1),
(2), (4) Date: May 31, 2005

(87) PCT Pub. No.: WO03/082866

PCT Pub. Date: Oct. 9, 2003

(65) Prior Publication Data

US 2006/0094740 A1   May 4, 2006
US 2007/0293527 A9   Dec. 20, 2007

Related U.S. Application Data

(60) Provisional application No. 60/369,347, filed on Apr. 3, 2002.

(30) Foreign Application Priority Data

Apr. 3, 2002   (FI) .................................. 20020642

(51) Int. Cl.
*A61K 31/4355*   (2006.01)
*C07D 491/12*   (2006.01)

(52) U.S. Cl. ..................... 514/285; 546/62; 546/47; 514/280

(58) Field of Classification Search ................ 514/285, 514/280; 546/62, 47
See application file for complete search history.

(56) References Cited

U.S. PATENT DOCUMENTS

| | | | |
|---|---|---|---|
| 3,203,860 A | 8/1965 | Wu et al. |
| 3,492,303 A | 1/1970 | Shavel et al. |
| 4,036,841 A | 7/1977 | Szántay et al. |
| 4,044,012 A | 8/1977 | Szántay et al. |
| 4,587,251 A | 5/1986 | Ezer et al. |
| 4,686,226 A | 8/1987 | Huff et al. |
| 4,710,504 A | 12/1987 | Baldwin et al. |
| 4,806,545 A | 2/1989 | Szántay et al. |
| 5,902,807 A | 5/1999 | Haapalinna et al. |

FOREIGN PATENT DOCUMENTS

| | | |
|---|---|---|
| EP | 0 089 926 A2 | 9/1983 |
| EP | 0 089 926 A3 | 9/1983 |
| EP | 0 130 823 A2 | 1/1985 |
| EP | 0 183 492 A1 | 6/1986 |
| EP | 0 204 254 A2 | 12/1986 |
| EP | 0 204 254 A3 | 12/1986 |
| EP | 0 213 793 A2 | 3/1987 |
| FR | 1 209 650 | 3/1960 |
| FR | 1524953 | 4/1968 |
| FR | 2 478 639 | 9/1981 |
| GB | 844342 | 8/1960 |
| GB | 983848 | 2/1965 |
| GB | 1003645 | 9/1965 |
| GB | 1 435 573 | 5/1976 |
| GB | 2 106 909 A | 4/1983 |
| WO | WO 99/28300 | 6/1999 |
| WO | WO 01/64645 | 9/2001 |

OTHER PUBLICATIONS

Joel R. Huff et al., "Structure-Affinity Relationships of Arylquinolizines at α-Adrenoceptors," J. Med. Chem., vol. 31, pp. 641-645, 1988.
C. Galvez et al., "A Revision of the Synthesis of some Polycyclic Systems Related to Benzoheteroquinolizidines," J. Heterocyclic Chem., vol. 17, pp. 1355-1357, 1980.
Ben E. Evans et al., "N-(1,3,4,6,7,12b-Hexahydro-2H-benzo[*b*]furo[2,3-*a*]quinolizin-2yl)-N-methyl-2-hydroxyethane-sulfonamide: A Potent and Selective α$_2$-Adrenoceptor Antagonist," J. Med. Chem., vol. 28, pp. 1756-1759, 1985.
Elaine J. Browne, "Synthesis of 1*H*-[1]Benzothieno[3,2-*d*]azonine and [1]Benzothieno[3,2-*d*]azecine Derivatives," Aust. J. Chem., vol. 38, pp. 765-776, 1985.

(Continued)

*Primary Examiner*—Charanjit S Aulakh
(74) *Attorney, Agent, or Firm*—Finnegan, Henderson, Farabow, Garrett & Dunner, LLP

(57) ABSTRACT

A compound of formula I,

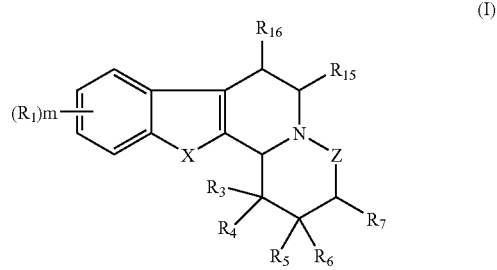

wherein X, Z, $R_1$ to $R_{10}$, $R_{15}$, $R_{16}$, m, n, r and t are as defined in claim 1, or a pharmaceutically acceptable salt or ester thereof, useful as an alpha-2 antagonist. The compounds of formula I can be used for the treatment of diseases or conditions where antagonists of alpha-2 adrenoceptors are indicated to be effective.

8 Claims, 5 Drawing Sheets

OTHER PUBLICATIONS

N. B. Chapman et al., "Some Polycyclic Systems related to [1]Benzothieno[2,3-c]pyridine," J. Chem. Soc., pp. 2269-2272, 1970.

Antti Haapalinna et al., "Evaluation of the effects of a specific $\alpha_2$-adenoceptor antagonist, atipamezole, on $\alpha_1$-and $\alpha_2$-adenoceptor subtype binding, brain neurochemistry and behaviour in comparison with yohimbine," Naunyn-Schmiedeberg's Arch Pharmacol, 356:570-582, 1997.

C. Szántay et al., "Synthesis of Vinca Alkaloids and Related Compounds-II+, Stereoselective and Enantioselective Synthesis of (+)-Vincamine," Tetrahedron, vol. 33, pp. 1803-1808, 1977.

Bruno Danieli et al., "A New Approach to (±)-Apovincamine", Gazzetta Chimica Italiana, 111, pp. 257-267, 1981.

György Kalaus et al., "Synthesis of Vinca Alkaloids and Related Compounds XXXV. Preparation of 1-Ethyl-Hydroxyethyl-Octahydroindolo[2,3-a]Quinolizine Derivatives and Reactions of Their Mesylates with Cyanide Ion," Heterocycles, vol. 27, No. 5, pp. 1179-1190, 1988.

Mauri Lounasmaa et al., "Easy Preparation of Indoloquinolizidine Enamines," Heterocycles, vol. 32, No. 3, pp. 489-497, 1991.

Denis Génin et al., "A Short Stereoselective Synthesis of the Alkaloid Vincamine," J. Org. Chem., vol. 52, pp. 353-356, 1987.

Edward Piers et al., "Synthesis of functionalized bicyclo[3.2.1]octa-2,6-dienes by thermal rearrangement of substituted 6-exo-(1-alkenyl)bicyclo[3.1.0]hex-2-ene systems," Can. J. Chem., vol. 65, pp. 670-682, 1987.

Joan-Carles Fernández et al., "A Straightforward Route to Ibophyllidine Alkaloids by a Double Transannular Cyclization," J. Chem. Soc., Chem. Commun., pp. 2317-2318, 1995.

M.S. Allen et al., "Preparation of 2-Acyl- and 2-Alkoxycarbonyl-octahydroindolo[2,3-a]-quinolizines," J. Chem. Soc. (C), pp. 736-743, 1971.

R. Iyer et al., "Electrophilic Substitution in 6-Methoxyindoles," J.C.S. Chem. Comm., pp. 461-462, 1972.

L. Damuynck et al., Rearrangement d'indolo[2,3-a]quinolizidiness en dérivée ã aqualatte B-azaagpidospermane, Tetrahedron Letters, vol. 30, No. 6, pp. 719-722, 1989.

Malcolm Sainsbury et al., Chemical and Photochemical Cyclisations of 1-Alkylidene-1,2,3,4-tetrahydro-2-nicotinoyl- and -isonicotinoyl-β-carbolines: A Regiospecific Synthesis of Nauclefine,: Journal of the Chemical Society, Perkin Transactions I., pp. 2109-2115, 1977.

Martin E. Kuehne et al., "Total Syntheses of Yohimbe Alkaloids, with Stereoselection for the Normal, Allo, and 3-Epiallo Series, Based on Annelations of 4-Methoxy-1,2-dihydropyridones," J. Org. Chem., vol. 56, pp. 2701-2712, 1991.

Heinz Rischke et al., "Steroselecktive Cyclisierungen in der Indolreihe," Chem. Ber., vol. 106, pp. 3106-3113, 1973.

Etsuji Yamanaka et al., "A New Indole Alkaloid, 14α-Hydroxyrauniticine: Structure Revision and Partial Synthesis," Chem. Pharm. Bull., 34(9)3713-3721, 1986.

Mauri Lounasmaa et al., "Stereoregulation of the C(12b)H-C(2)H Relationship in the Preparation of 2-Substituted 1,2,3,4,6,7,12,12b-Octahydro-Indolo[2,3-a]Quinolizines," Tetrahedron, vol. 45, No. 12, pp. 3975-3992, 1989.

Lionel Chevolot et al., "XII (*)—Synthéses d'alcaloides indoliques et d'analogues structuraux par l'intermédiaire de sels de dihydro-5,6 pyridinium," Bulletin De La Société Chimique De France, No. 7-8, pp. 1222-1226, 1976.

Mauri Lounasmaa et al., "Stereoregulation of the Preparation of 1- and 3-Monosubstituted 1,2,3,4,6,7,12,12b-Octahydroindolo[2,3-a]Quinolizines," Tetrahedron, vol. 45, No. 23, pp. 7615- 7630, 1989.

T.R. Govindachari et al., "A Formal Synthesis of (±)-Vincamine," Indian Journal of Chemistry, vol. 22B, pp. 531-537, 1983.

Mauri Lounasmaa et al., "Stereochemical Course of the Alkaline Decarboalkoxylative Cyclization of C(4)-, C(5)-, and C(4),C(5)-Substituted 1-[2-(3-Indolyl)Ethyl]-3-Methoxycarbonyl-1,4,5,6-Tetrahydropyridines to C(2)-, C(3)- and C(2), C(3)- Substituted Indolo[2,3-a]Quinolizidines," Tetrahedron, vol. 46, No. 7, pp. 2633-2650, 1990.

S.B. Mandal et al., "Reduction of Lactams and Thiolactams by Sodium Borohydride: Application in the Synthesis of Some Alkaloids," J. Org. Chem., vol. 53, pp. 4236-4241, 1988.

Mauri Lounasmaa et al., "Acid-Catalysed Epimerization of 1-Substituted Indolo[2,3-a]quinolizidines: Stereoselective Routes to cis- and trans-Deethyleburnamonine Starting from the Same Ester Intermediate," Tetrahedron, vol. 52, No. 29, pp. 9925-9930, 1996.

Robert N. Schut et al., "The Enamine Chemistry of 2,3,4,6,7,12-Hexahydroindolo[2,3-a]quinolizine. Reaction with a,β-Unsaturated Aldehydes and Ketones," The Journal of Organic Chemistry, vol. 34, pp. 330-333, No. 2, 1969.

György Kalaus et al., "Synthesis of Vinca Alkaloids and Related Compounds. Part 74. Reaction of (±)-1a-Ethyl-1α-(mesyloxymethyl)-1,2,3,4,6,7,12,12bβ-octahydroindolo[2,3-a]quinolizine with Hydride and N Nucleophiles," J. Chem. Research (S), 382, 1995.

Mauri Lounasmaa et al., "Stereoselective Preparation of Indoloquinolizidine N-Oxides: Predominant Conformations," Tetrahedron, Vol. 47, No. 16, pp. 2879-2894, 1991.

Jeffrey R. Jasper et al., "Ligand Efficacy and Potency at Recombinant $\alpha_2$ Adrenergic Receptors," Biochemical Pharmacology, vol. 55, pp. 1035-1043, 1998.

M. Scheinin et al., "Evaluation of the $\alpha_{2C}$-adrenoceptor as a neuropsychiatric drug target Studies in transgenic mouse models," Life Sciences vol. 68, pp. 2277-2285, 2001.

J.C. Hunter et al., "Assessment of the role of $\alpha_2$-adrenoceptor subtypes in the antinociceptive, sedative and hypothermic action of dexmedetomidine in transgenic mice," British Journal of Pharmacology, vol. 122, pp. 1339-1344, 1997.

Neal R. Swerdlow, et al., "Assessing the Validity of an Animal Model of Deficient Sensorimotor Gating in Schizophrenic Patients," Arch. Gen. Psychiatry, vol. 51, 1994, pp. 139-159.

David L. Braff et al., "Human studies of prepulse inhibition of startle: normal subjects, patient groups, and pharmacological studies," Psychopharmacology, 156:234-258, 2001.

Robert R. Ruffolo, Jr. et al., "Pharmacologic and Therapeutic Applications of $\alpha_{2C}$-Adrenoceptor Subtypes," Annual Reviews Inc., pp. 243-281, 1993.

Renate Griffith et al., "Modelling of adrenoceptor ligand targets based on novel medium- or macro-sized fused nitrogen heterocyclic systems," Journal of Computer-Aided Molecular Design, 13:69-78, 1999, with Abstract.

Ekkehard Bölsing et al., "Ein stereoselektiver Zugang zu Isoeburnamonin," Chem. Ber. vol. 114, pp. 1932-1937, 1981.

S.H. Poghossian et al., "Indole Derivatives," Armyanskii Khimicheskii Zhurnal, vol. 31, No. 4, pp. 260-266, 1978, with Abstract.

Ahmed O. Abdel-Zaher et al., "The Potential Antidiabetic Activity of Some Alpha-2 Adrenoceptor Antagonists," Pharmacological Research, vol. 44, No. 5, 2001, including Abstract.

Riku Aantaa, "Alpha$_2$-adrenoceptor antagonists," Bailliere's Clinical Anaesthesiology, vol. 14, No. 2, pp. 285-292, 2000, with Abstract.

A.T. Guay et al., "Yohimbine treatment of organic erectile dysfunction in a dose-escalation trial," International Journal of Impotence Research, vol. 14, pp. 25-31, 2002, with Abstract.

S.A. Pogosyan et al., "Indole derivatives LX 1,2,3,4,4a,5,7,8,13b,13c-Decahydro-13H-benz[g]indolo[2,3-a]indolizines and 1,2,3,4,4a,5,7,8,9,14,14b,14c-dodecahydroisoindolo[1,2-a]indolo[2,3-c]azepines," Abstract, AN 1978: 59770 CAPLUS, DN 89:19770.

Ekkehard Boelsing et al., "Reactions of indole derivatives. XLVI. Steroselective route to isoeburnamonine," Abstract, AN 1981: 533210 CAPLUS, DN 95: 133210.

Derwent Abstract of EP 0 089 926 A3.

Derwent Abstract of FR 2 478 639.

J.C. Winter et al., "Synthesis of Some 3-Indenealkylamines. Comparison of the Biological Activity of 3-Indenealkylamines and 3-Benzo(b)thiophenealkylamines with Their Tryptamine Isosteres," Journal of Medicinal Chemistry, 10(5), pp. 856-859, 1967.

POLYCYCLIC COMPOUNDS AS POTENT ALPHA2-ADRENOCEPTOR ANTAGONISTS

This application is a U.S. national stage filing of PCT international application no. PCT/FI03/00255, filed on Apr. 3, 2003, which claims the benefit of priority to Finnish patent application no. 20020642, filed on Apr. 3, 2002 and U.S. provisional application No. 60/369,347, filed on Apr. 3, 2002.

FIELD OF THE INVENTION

The present invention relates to pharmacologically active arylquinolizine derivatives and related compounds and to their pharmaceutically acceptable salts and esters thereof, as well as to pharmaceutical compositions containing them and to their use as alpha2 antagonists.

BACKGROUND OF THE INVENTION

Some compounds exhibiting alpha adrenergic activity are well known in the art. It is also generally known and accepted in the art that those compounds may be used for the treatment of a wide variety of diseases and conditions of the peripheric system and the central nervous system (CNS).

The alpha adrenergic receptors can be divided on a pharmacological basis into alpha1- and alpha2-adrenoceptors, which can both be further divided into subtypes. Three genetically encoded subtypes, namely alpha2A-, alpha2B- and alpha2C-adrenoceptors, have been discovered in human. Accordingly, alpha2-adrenoceptors in humans have been subdivided into three pharmacological subtypes known as alpha2A-, alpha2B- and alpha2C-adrenoceptors. A fourth, pharmacologically defined subtype, alpha2D, is known in rodents and in some other mammals, and it corresponds to the genetically defined alpha2A-adrenoceptors.

The alpha2-adrenoceptor subtypes have distinct tissue distributions and functional roles. For instance, while alpha2A-adrenoceptors are widely expressed in various tissues, alpha2C-adrenoceptors are concentrated in the CNS, and they appear to play a role in the modulation of specific CNS-mediated behavioural and physiological responses.

Compounds that are non-specific to any of the above-mentioned alpha2 subtypes, and compounds that are specific to certain alpha2 subtypes, are already known. For example, atipamezole is a non-specific alpha2 antagonist. Atipamezole has been described in, for example, EP-A-183 492 (cf. p. 13, compound XV) and Haapalinna, A. et al., *Naunyn-Schmiedeberg's Arch. Phannacol.* 356 (1997) 570-582. U.S. Pat. No. 5,902,807 describes compounds that are selective antagonists for the alpha2C subtype and may be used in the treatment of mental illness, e.g. mental disturbance induced by stress. Such compounds include, for example, MK-912 and BAM-1303. Furthermore, WO-A-99 28300 discloses substituted imidazole derivatives having agonist-like activity for alpha2B- or 2B/2C-adrenoceptors. In addition, WO 01/64645 relates to derivatives of quinoline useful as alpha2 antagonists, as well as to selective alpha2C antagonist agents. The disclosures of all documents cited above in this paragraph are incorporated by reference herein.

Several arylquinolizine derivatives and related compounds have been described in the literature, some of which possess valuable pharmaceutical effects. For example, U.S. Pat. Nos. 4,806,545 and 4,044,012 describe 1,1-disubstituted indolo[2,3-a]quinolizidines useful as vasodilators and antihypoxic agents. Further, substituted arylquinolizine derivatives, described for example in U.S. Pat. No. 4,686,226 possessing alpha2-adrenoceptor antagonistic activity are useful for example as antidepressant, antihypertensive, or antidiabetic agents or platelet aggregation inhibitors. In addition, U.S. Pat. No. 3,492,303 relates to indolo[2,3-a]quinolizidines useful as central nervous system depressants. Molecular modelling of targets for synthesis of alpha1A and alpha2 selective ligands is discussed in Griffith, R. et al., *J. Comput.-Aided Mol. Design* 13 (1999) 69-78.

SUMMARY OF THE INVENTION

An object of the present invention is to provide further antagonists of alpha2-adrenoceptors that can be used for the treatment of diseases or conditions of the peripheric or central nervous system where alpha2-antagonists are indicated to be useful. Accordingly, an object of the present invention is to provide further compounds to be used as alpha2 antagonist agents in the treatment of mammals, including humans and animals.

The invention also provides compounds usefuil as selective alpha2C antagonist agents for the treatment of various disorders or conditions of the central nervous system where alpha2C antagonists are indicated to be useful.

DETAILED DESCRIPTION OF THE INVENTION

Figure 1B:
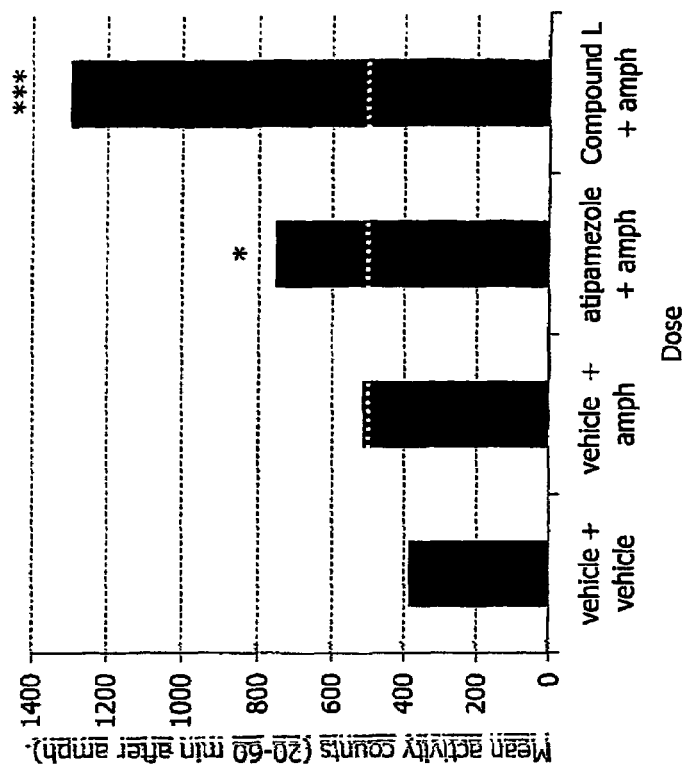
FIGS. 1a and b show the results from two separate locomotor activity tests where the locomotor activity of mice was tested after injections of vehicle or amphetamine (amph) (4 micromol/kg). The mice were pre-treated (20 min before amphetamine) either with vehicle, the subtype non-selective alpha2-antagonist atipamezole (1 micromol/kg) or the alpha2C-antagonists, compound K (3 micromol/kg)(FIG. a) or compound L (3 micromol/kg)(FIG. b). * $p<0.05$,  $p<0.01$ and * $p<0.001$ compared to vehicle+amph -group (1-way ANOVA+LSD -test).

One embodiment of the present invention covers the use of compounds of formula I,

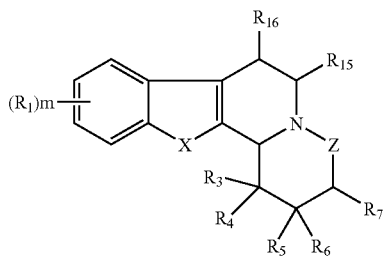

I wherein,

X is $CR_2R_2'$, O, S or $NR_2$;

Z is —$CHR_8$—$(CH_2)n$- or a single bond;

$R_1$ is hydroxy, $(C_1-C_6)$alkyl, $(C_1-C_6)$alkoxy, halogen, halo$(C_1-C_6)$alkyl, $(C_1-C_6)$alkoxy-CO—, CN, $NO_2$, $NH_2$, mono- or di$(C_1-C_6)$alkylamino or carboxyl;

$R_2$ and $R_2'$ are independently H, hydroxy or $(C_1-C_6)$alkyl or $R_2$ and $R_2'$ form, together with the carbon ring atoms to which they are attached, a carbonyl group;

$R_3$ is H, hydroxy, $(C_1-C_6)$alkyl, $(C_2-C_6)$alkenyl, hydroxy$(C_1-C_6)$alkyl, $(C_1-C_6)$alkoxy, $(C_1-C_6)$alkoxy$(C_1-C_6)$alkyl, hydroxy$(C_1-C_6)$alkoxy$(C_1-C6)$alkyl, $(C_3-C_7)$cycloalkyl, $(C_3-C_7)$cycloalkyl$(C_1-C_6)$alkyl, aryl, aryl$(C_1-C_6)$alkyl, aryloxy, aryl$(C_1-C_6)$alkoxy, aryloxy$(C_1-C_6)$alkyl, aryl$(C_1-C_6)$alkoxy$(C_1-C_6)$alkyl, halo$(C_1-C_6)$alkyl, NH2, amino$(C_1-C_6)$alkyl, mono- or di$(C_1-C_6)$alkylamino,mono- or di$(C_1-C_6)$alkylamino$(C_1-C_6)$alkyl, $(C_1-C_6)$alkyl-CO—, $(C_1-C_6)$alkyl-CO—O—, $(C_1-C_6)$alkyl-CO—O—$(C_1-C_6)$alkyl, $(C_1-C_6)$alkoxy-CO—, $(C_1-C_6)$alkoxy-CO—$(C_1-C_6)$alkyl, $(C_1-C_6)$alkoxy-CO—$(C_1-C_6)$alkoxy$(C_1-C_6)$alkyl, carbamoyl, mono- or di$(C_1-C_6$alkylcarbamoyl, carboxyl or $(C_1-C_6)$alkyl-S—$(C_1-C_6)$alkyl, wherein the said $(C_3-C_7)$cycloalkyl or aryl is unsubstituted or substituted with 1 or 2 substituents each independently being hydroxy, $(C_1-C_6)$alkyl, halogen, $(C_1-C_6)$alkoxy, $NH_2$, CN or $NO_2$, or one of $R_3$ or $R_4$ and $R_6$ together form a bond between the ring atoms to which they are attached;

$R_4$ is H, hydroxy, $(C_1-C_6)$alkyl, hydroxy$(C_1-C_6)$alkyl, $(C_1-C_6)$alkoxy or $(C_1-C_6)$alkoxy$(C_1-C_6)$alkyl;

$R_5$ is H, hydroxy, $(C_1-C_6)$allyl, $(C_2-C_6)$alkenyl, $(C_1-C_6)$alkoxy, $(C_1-C_6)$alkoxy$(C_1-C_6)$alkyl, $(C_3-C_7)$cycloalkyl, $(C_3-C_7)$cycloalkyl$(C_1-C_6)$alkyl, aryl, aryl$(C_1-C_6)$alkyl, aryloxy, aryl$(C_1-C_6)$alkoxy, aryloxy$(C_1-C_6)$alkyl, aryl$(C_1-C_6)$alkoxy$(C_1-C_6)$alkyl, halo$(C_1-C_6)$alkyl, $(C_1-C_6)$alkyl-CO—O—, $(C_1-C_6)$alkyl-CO—O—$(C_1-C_6)$alkyl, $(C_1-C_6)$alkoxy-CO—$(C_1-C_6)$alkoxy$(C_1-C_6)$alkyl, carbamoyl, mono- or di$(C_1-C_6)$alkylcarbamoyl, carboxyl or $(C_1-C_6)$alkyl-S—$(C_1-C_6)$alkyl, wherein the said $(C_3-C_7)$cycloalkyl or aryl is unsubstituted or substituted with 1 or 2 substituents each independently being hydroxy, $(C_1-C_6)$alkyl, halogen, $(C_1-C_6)$alkoxy, $NH_2$, CN or $NO_2$, or $R_4$ and $R_5$ form, together with the carbon ring atoms to which they are attached, a condensed five to seven membered saturated carbocyclic ring substituted with 1 to 3 substituent(s) $R_9$ each independently being hydroxy, $(C_1-C_6)$alkyl, halogen, $NH_2$, $NO_2$, $(C_3-C_7)$cycloalkyl, hydroxy$(C_1-C_6)$alkyl, halo$(C_1-C_6)$alkyl, amino$(C_1-C_6)$alkyl, mono- or di$(C_1-C_6)$alkylamino, mono- or di$(C_1-C_6)$alkylamino$(C_1-C_6)$alkyl, $(C_1-C_6)$alkoxy, $(C_1-C_6)$alkoxy$(C_1-C_6)$alkyl, carboxyl, $(C_1-C_6)$alkyl-CO—, $(C_1-C_6)$alkyl-CO—O—, $(C_1-C_6)$alkoxy-CO—, $(C_1-C_6)$alkoxy-CO—$(C_1-C_6)$alkyl, carbamoyl mono- or di$(C_1-C_6)$alkylcarbamoyl or oxo;

$R_6$ is H, hydroxy, $(C_1-C_6)$alkyl, $(C_1-C_6)$alkoxy or $(C_1-C_6)$alkoxy$(C_1-C_6)$alkyl or $R_6$ forms a bond between the ring atom to which it is attached and the ring atom to which $R_7$ is attached;

$R_7$ is H, hydroxy, $(C_1-C_6)$alkyl, hydroxy$(C_1-C_6)$atkyl, $(C_1-C_6)$alkoxy or $(C_1-C_6)$alkoxy$(C_1-C_6)$alkyl;

$R_8$ is H,hydroxy, $(C_1-C_6)$alkyl, hydroxy$(C_1-C_6)$alkyl, $(C_1-C_6)$alkoxy or $(C_1-C_6)$alkoxy$(C_1-C_6)$alkyl or, only when n is 0, $R_7$ and $R_8$ form, together with the carbon ring atoms to which they are attached, a condensed five to seven membered saturated carbocyclic ring unsubstituted or substituted with 1 to 3 substituent(s) $R_{10}$ each independently being hydroxy, $(C_1-C_6)$alkyl, halogen, $NH_2$, $NO_2$, $(C_3-C_7)$cycloalkyl, hydroxy$(C_1-C_6)$alkyl, halo$(C_1-C_6)$alkyl, amino$(C_1-C_6)$alkyl, mono- or di$(C_1-C_6)$alkylamino, mono- or di$(C_1-C_6)$alkylamino$(C_1-C_6)$alkyl, $(C_1-C_6)$alkoxy, $(C_1-C_6)$alkoxy$(C_1-C_6)$alkyl, carboxyl, $(C_1-C_6)$alkyl-CO—, $(C_1-C_6)$alkyl-CO—O—, $(C_1-C_6)$alkoxy-CO—, $(C_1-C_6)$alkoxy-CO—$(C_1-C_6)$alkyl, carbamoyl, mono- or di$(C_1-C_6)$alkylcarbamoyl or oxo;

$R_{15}$ is H, $(C_1-C_6)$alkyl, $(C_2-C_6)$alkenyl, hydroxy$(C_1-C_6)$alkyl, $(C_1-C_6)$alkoxy$(C_1-C_6)$alkyl, hydroxy$(C_1-C_6)$alkoxy$(C_1-C_6)$alkyl, halo$(C_1-C_6)$alkyl, amino$(C_1-C_6)$alkyl, mono- or di$(C_1-C_6)$alkylamino$(C_1-C_6)$alkyl, $(C_1-C_6)$alkyl-CO—, $(C_1-C_6)$alkyl-CO—O—$(C_1-C_6)$alkyl, $(C_1-C_6)$alkoxy-CO—, $(C_1-C_6)$alkoxy-CO—$(C_1-C_6)$alkyl, $(C_1-C_6)$alkoxy-CO—$(C_1-C_6)$alkoxy$(C_1-C_6)$alkyl, carbamoyl, mono- or di$(C_1-C_6)$alkylcarbamoyl or carboxyl;

$R_{16}$ is H or $(C_1-C_6)$alkyl;

$R_7$ and $R_8$ are attached to the carbon ring atoms, which are adjacent;

m is 0 to 2; and n is 0 or 1, or a pharmaceutically acceptable salt or ester thereof, with the proviso, that the compound is not 1,2,3,4,5,10b-hexahydro-10-thia-3a-aza-cyclopenta[a]fluorine, for the manufacture of a medicament for the treatment of diseases or conditions where alpha2 antagonists are indicated to be effective.

In a possible subgroup of the compounds of formula I X is $NR_2$.

In another possible subgroup of the compounds of formula I m is 0, n is 0, $R_2$ is H, $R_3$ is H, hydroxy, $(C_1-C_6)$alkyl, hydroxy$(C_1-C_6)$alkyl, $(C_1-C_6)$alkoxy$(C_1-C_6)$alkyl, $(C_3-C_7)$cycloalkyl, halo$(C_1-C_6)$alkyl, $(C_1-C_6)$alkyl-CO—, $(C_1-C_6)$alkyl-CO—O—$(C_1-C_6)$alkyl, $(C_1-C_6)$alkoxy-CO—or $(C_1-C_6)$alkoxy-CO—$(C_1-C_6)$alkyl, $R_4$ is H, hydroxy, $(C_1-C_6)$alkyl or hydroxy$(C_1-C_6)$alkyl, $R_5$ is H, hydroxy, $(C_1-C_6)$alllyl or $(C_1-C_6)$alkoxy, $R_6$ is H or $(C_1-C_6)$alkyl and $R_7$ is H, $(C_1-C_6)$alkyl or hydroxy$(C_1-C_6)$alkyl.

In another possible subgroup of the compounds of formula I $R_3$ is H or $(C_1-C_6)$alkyl and $R_4$ is hydroxy or hydroxy$(C_1-C_6)$alkyl.

In another possible subgroup of the compounds of formula I $R_4$ and $R_5$ form, together with the carbon ring atoms to which they are attached, a condensed six membered saturated carbocyclic ring.

In another possible subgroup of the compounds of formula I $R_4$ and $R_6$ together form a bond between the ring atoms to which they are attached or $R_6$ forms a bond between the ring atom to which it is attached and the ring atom to which $R_7$ is attached.

In a further possible subgroup of the compounds of formula I the compound is 1α-ethyl-1,2,3,4,6,7,12,12bβ-octahydro-indolo[2,3-a]quinolizin-1-ol, (1β-ethyl-1,2,3,4,6,7,12,12bα-octahydro-indolo[2,3-a]quinolizin-1-yl)-methanbl, 1α-Methyl-1,2,3,4,6,7,12,12bβ-octahydroindolo[2,3-a]

quinolizin-1-ol, (1α-Methyl-1,2,3,4,6,7,12,12bβ-octahydroindolo[2,3-a]quinolizin-1-yl)-methanol or 3,4,4aβ,5,6,7,8,13,13bβ,13cα-decahydro-2H-6a,13-diaza-indeno[1,2-c]phenanthren-1-one.

In another possible subgroup of the compounds of formula I X is $CR_2R_2'$.

In a further possible subgroup of the compounds of formula I X is S.

In yet another possible subgroup of the compounds of formula I X is O.

When X is O, one possible subgroup of the compounds of formula I includes $R_5$ and $R_3$ as defined in the description of the use of the compounds of formula I above.

Another possible subgroup of the compounds of formula I when X is O is where $R_5$ is H, hydroxy, $(C_1-C_6)$alkyl, $(C_2-C_6)$alkenyl, $(C_1-C_6)$alkoxy, $(C_1-C_6)$alkoxy$(C_1-C_6)$alkyl, $(C_3-C_7)$cycloalkyl, $(C_3-C_7)$cycloalkyl$(C_1-C_6)$alkyl, aryl, aryl$(C_1-C_6)$alkyl, aryloxy, aryl$(C_1-C_6)$alkoxy, aryloxy$(C_1-C_6)$alkyl, aryl$(C_1-C_6)$alkoxy$(C_1-C_6)$alkyl, halo$(C_1-C_6)$alkyl, $(C_1-C_6)$alkyl-CO—O—, $(C_1-C_6)$alkyl-CO—O—$(C_1-C_6)$alkyl, $(C_1-C_6)$alkoxy-CO—$(C_1-C_6)$alkoxy$(C_1-C_6)$alkyl, carbamnoyl, mono- or di$(C_1-C_6)$alkylcarbamoyl, carboxyl or $(C_1-C_6)$alkyl-S—$(C_1-C_6)$alkyl and $R_6$ is H, hydroxy, $(C_1-C_6)$alkyl, $(C_1-C_6)$alkoxy or $(C_1-C_6)$alkoxy$(C_1-C_6)$alkyl.

Another embodiment of the invention provides new compounds of formula IA:

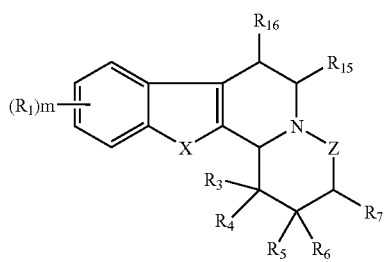

IA wherein,
X is $CR_2R_2'$, O or S;
Z, $R_1$, $R_2$, $R_2'$, $R_3$-$R_{10}$, $R_{15}$ and $R_{16}$, m and n are as defined in claim 1, or a pharmaceutically acceptable salt or ester thereof, with the provisos, that
a) when X is O, m is 0 and n is 0, then $R_3$-$R_8$ are not all simultaneously hydrogen;
b) the compound is not 1,2,3,4,5,10b-hexahydro-10-thia-3a-aza-cyclopenta[a]fluorene; 1,3,4,5,6,11b-hexahydro-2H-11-thia-4a-aza-benzo[a]fluorene; 1-(1,3,4,5,6,11b-hexahydro-2H-11-thia-4a-aza-benzo[a]fluoren-1-yl)-ethanone or 1,3,4,5,6,11b-hexahydro-2H-11-thia-4a-aza-benzo[a]fluorene-1-carboxylic acid methyl ester; for example
wherein X is $CR_2R_2'$; or
wherein X is O; or
wherein X is S; or
wherein $R_3$ is hydroxy, $(C_1-C_6)$alkyl, hydroxy$(C_1-C_6)$alkyl, $(C_1-C_6)$alkoxy$(C_1-C_6)$alkyl, $(C_1-C_6)$alkoxy-CO— or $(C_1-C_6)$alkyl-CO—O—$(C_1-C_6)$alkyl and $R_4$ is H, $(C_1-C_6)$alkyl or hydroxy$(C_1-C_6)$alkyl; or
wherein $R_3$ is hydroxy, hydroxy$(C_1-C_6)$alkyl or $(C_1-C_6)$alkoxy$(C_1-C_6)$alkyl and $R_4$ is $(C_1-C_6)$alkyl; or
wherein $R_4$ and $R_5$ form, together with the carbon ring atoms to which they are attached, a condensed six membered saturated carbocyclic ring; or wherein the compound is 1α-Methyl-1,3,4,5,6,11b-hexahydro-2H-11-oxa4a-aza-benzo[a]fluoren-1-ol, (1α-Methyl-1,3,4,5,6,11bβ-hexahydro-2H-11-oxa-4a-aza-benzo[a]fluoren-1-yl)-methanol, (−)-(1α-Methyl-1,3,4,5,6,11bβ-hexahydro-2H-11-oxa-4a-aza-benzo[a]fluoren-1-yl)-methanol, (+)-(1α-Methyl-1,3,4,5,6,11bβ-hexahydro-2H-11-oxa-4a-aza-benzo[a]fluoren-1-yl)-methanol, 1α-Isopropyl-1,3,4,5,6,11b-Hexahydro-2H-11-oxa-4a-aza-benzo[a]fluoren-1-ol, 1α-Ethyl-1,3,4,5,6,11bβ-hexahydro-2H-11-oxa-4a-aza-benzo[a]fluoren-1-ol, (1α-Ethyl-1,3,4,5,6,11bβ-hexahydro-2H-11-oxa-4a-aza-benzo[a]fluoren-1-yl)-methanol, 1-Methyl-1α,3,4,6,11bβ-hexahydro-2H-11-oxa-4a-aza-benzo[a]fluorene, (1-Hydroxymethyl-1,3,4,5,6,11b-hexahydro-2H-11-oxa-4a-aza-benzo[a]fluoren-1-yl]-methanol, 1-Methoxymethyl-1α-methyl-1,3,4,5,6,11bβ-hexahydro-2H-11-oxa-4a-aza-benzo[a]fluorene, (−)-1-Methoxymethyl-1α-methyl-1,3,4,5,6,11bβ-hexahydro-2H-11-oxa-4a-aza-benzo[a]fluorene, (+)-1-Methoxymethyl-1α-methyl-1,3,4,5,6,11bβ-hexahydro-2H-11-oxa-4a-aza-benzo[a]fluorene, 1α-Methyl-1,3,4,5,6,11bα-hexahydro-2H-11-oxa-4a-aza-benzo[a]fluorene-1-carboxylic acid ethyl ester, 1-Ethoxymethyl-1α-methyl-1,3,4,5,6,11bβ-hexahydro-2H-11-oxa-4a-aza-benzo[a]fluorene, (1α-Methyl-1,3,4,5,6,11bα-hexahydro-2H-11-oxa-4a-aza-benzo[a]fluoren-1-yl)-methanol, (−)-(1α-Methyl-1,3,4,5,6,11bα-hexahydro-2H-11-oxa-4a-aza-benzo[a]fluoren-1-yl)-methanol, (+)-(1α-Methyl-1,3,4,5,6,11bα-hexahydro-2H-11-oxa-4a-aza-benzo[a]fluoren-1-yl)-methanol, 1α-Ethyl-1,3,4,5,6,11bα-hexahydro-2H-11-oxa-4a-aza-benzo[α]fluorene-1-carboxylic methyl ester, 1-Methoxymethyl-1α-methyl-1,3,4,5,6,11bα-hexahydro-2H-11-oxa-4a-aza-benzo[a]fluorene, (−)-1-Methoxymethyl-1α-methyl-1,3,4,5,6,11bα-hexahydro-2H-11-oxa-4a-aza-benzo[a]fluorene, (+)-1-Methoxymethyl-1α-methyl-1,3,4,5,6,11bα-hexahydro-2H-11-oxa4a-aza-benzo[a]fluorene, (1α-Ethyl-1,3,4,5,6,11bα-hexahydro-2H-11-oxa-4a-aza-benzo[a]fluorene-1-yl)-methanol, acetic acid 1α-Methyl-1,3,4,5,6,11bβ-hexahydro-2H-11-oxa-4a-aza-benzo[a]fluoren-1-ylmethyl ester or (1α-Methyl-1,2,3,4,6,7,12,12bα-octahydroindeno[2,1-a]quinolizin-1-yl)-methanol.

Another embodiment of the invention provides new compounds of formula IB:

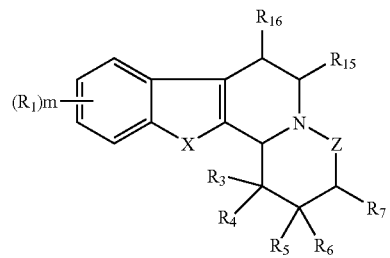

IB wherein,
X is $NR_2$;
$R_2$ is $(C_1-C_6)$alkyl;
Z, $R_1$, $R_3$-$R_{10}$, $R_{15}$, $R_{16}$, m and n are as defined in claim 1, or a pharmaceutically acceptable salt and ester thereof, with the provisos, that
a) when m is 0 or $R_1$ is methoxy and $R_4$ is H or ethyl, then $R_3$ is not methoxy-CO;
b) the compound is not 12-Methyl-1,2,3,4,6,7,12,12b-octahydro-indolo[2,3-a]quinolizine; 1-Ethyl-12-methyl-1,2,3,4,6,7,12,12b-octahydro-indolo[2,3-a]quinolizine;

2,3-Diethyl-12-methyl-1,2,3,4,6,7,12,12b-octahydro-indolo[2,3-a]quinolizine; 12-Methyl-1,2,3,4,6,7,12,12b-octahydro-indolo[2,3-a]quinolizin-1-ol; 2-(1-Ethyl-12-methyl-1,2,3,4,6,7,12,12b-octahydro-indolo[2,3-a]quinolizin-1-yl)-ethanol; 11-Methyl-2,3,5,6,11,11b-hexahydro-1H-indolizino[8,7-b]indole; (11-Methyl-2,3,5,6,11,11b-hexahydro-1H-indolizino[8,7-b]indol-1-yl)-methanol; (1,11-Diethyl-2,3,5,6,11,11b-hexahydro-1H-indolizino[8,7-b]indol-1-yl)-methanol or 3-(1-ethyl-12-methyl-1,2,3,4,6,7,12,12b-octahydro-indolo[2,3-a]quinolizin-1-yl)-propionic acid methyl ester; for example wherein $R_3$ is hydroxy, $(C_1-C_6)$alkyl, hydroxy$(C_1-C_6)$alkyl or $(C_1-C_6)$alkoxy$(C_1-C_6)$alkyl and $R_4$ is H, $(C_1-C_6)$alkyl or hydroxy$(C_1-C_6)$alkyl; or wherein the compound is 1α-Ethyl-12-methyl-1,2,3,4,6,7,12β-octahydro-indolo[2,3-a]quinolizin-1-ol or 1α-Ethyl-12-ethyl-1,2,3,4,6,7,12β-octahydro-indolo[2,3-a]quinolizin-1-ol.

Another embodiment of the invention provides new compounds of formula IC:

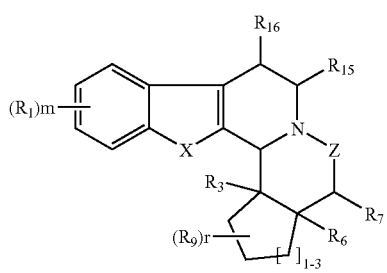

IC wherein,
X is $NR_2$;
$R_2$ is H;
Z is —$CHR_8$—$(CH_2)n$- or a single bond;
n is 0,
$R_1$, $R_3$, $R_6$-$R_9$, $R_{15}$, $R_{16}$ and m are as defined in claim 1;
r is 1 to 3;
or a pharmaceutically acceptable salt and ester thereof, with the provisos, that the compound is not 10-methyl-5,7,7a,8,9,10,11,11a,11b,12-decahydro-6H-6a,12-diaza-indeno[1,2-a]fluorene; 3-hydroxy-1,2,3,4,4a,5,6,7,8,13,13b, 13c-dodecahydro-6a,13-diaza-indeno[1,2-c]phenanthrene-4-carboxylic acid methyl ester; methyl-3-ethyl-1,2,3a,4,6,7,12b,12c-octahydro-3H, 12H-indolo[2,3-g]cyclopent[a]indolizine-2-carboxylate; methyl-1,2,3a,4,6,7,12b,12c-octahydro-3H,12H-indolo[2,3-g]cyclopent[a]indolizine-2-carboxylate or 12c-ethyl-1,3a,4,6,7,12b,12c-octahydro-cyclopent[1,2]indolizino[8,7-b]indol-3(2H)-one; for example wherein r 1 and $R_3$ is H, hydroxy, $(C_1-C_6)$ or hydroxy$(C_1-C_6)$alkyl; or wherein the compound is 3,4,4aβ,5,6,7,8,13,13bβ,13cα-decahydro-2H-6a,13-diaza-indeno[1,2-c]phenanthren-1-one, 1,2,3,4,5,6,7,8,13,13b-decahydro-6a,13-diaza-indeno[1,2-c]phenanthrene, acetic acid 1α,2,3,4,4αβ,5,6,7,8,13,13bβ,13cα-dodecahydro-6a,13-diaza-indeno[1,2-c]phenanthren-1-yl ester or acetic acid 1β,2,3,4,4αβ,5,6,7,8, 13,13bβ,13cα-dodecahydro-6a,13-diaza-indeno[1,2-c]phenanthren-1-yl ester.

Another embodiment of the invention provides new compounds of formula ID:

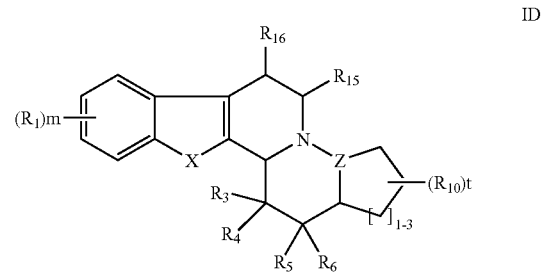

ID wherein,
X is $NR_2$;
$R_2$ is H;
Z is —CH—$(CH_2)n$-;
n is 0;
$R_1$, $R_3$-$R_{10}$ $R_{15}$, $R_{16}$ and m are as defined in claim 1;
t is 0 to 3;
or a pharmaceutically acceptable salt and ester thereof, with the provisos, that the compound is not 1,2,3,4,4a,5,6,11,11b,12,13,13a-dodecahydro-4b,11-diaza-indeno[2,1-a]phenanthrene; 1,2,3,4,4a,5,6,11,11b,12-decahydro-4b,11-diaza-indeno[2,1-a]phenanthrene; 9-methoxy- 1,2,3,4,4a,5,6,11,11b,12-decahydro-4b,11-diaza-indeno[2,1-a]phenanthrene or 1-hydroxy-1,2,3,4,4a,5,6,11,11b,12,13,13a-dodecahydro-4b,11-diaza-indeno[2,1-a]phenanthrene-2-carboxylic acid methyl ester.

Another embodiment of the invention provides new compounds of formula IE:

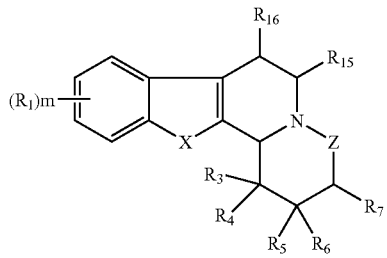

IE wherein,
X is $NR_2$;
$R_2$ is H;
Z, $R_1$, $R_3$-$R_{10}$, $R_{15}$, $R_{16}$ and m are as defined in claim 1;
n is 1,
or a pharmaceutically acceptable salt aid ester thereof, with the proviso, that the compound is not 2,3,4,5,7,8,13,13b-octahydro-2,3-diethyl-1H-azepino[1',2':1,2]pyrido[3,4-b]indole; acetic acid 2,3,4,5,7,8,13,13b-octahydro-1H-azepino[1',2':1,2]pyrido[3,4-b]indol-2-ylmethyl ester; 2,3,4,5,7,8,13,13b-octahydro-1H-azepino[1',2':1,2]pyrido[3,4-b]indole-2-[(phenylmethoxy)methyl] or 2,3,4,5,7,8,13,13b-octahydro-1H-azepino[1',2':1,2]pyrido [3,4-b]indole-4-ethyl-2-[(phenylmethoxy)methyl]; for example wherein the compound is 2,3,4,5,7,8,13,13b-Octahydro-1H-azepino[1',2': 1,2]pyrido[3,4-b]indole.

Another embodiment of the invention provides new compounds which are 2β-Methoxy-1,2,3,4,6,7,12,12bα-octahydro-indolo[2,3-a]quinolizine, 2α-methoxy-1,2,3,4,6,7,12, 12bα-octahydro-indolo[2,3-a]quinolizine, 1α-Ethyl-2α-methyl-1,2,3,4,6,7,12,12bβ-octahydro-indolo[2,3-a]quinolizin-1-ol, 1α-Isopropyl-1,2,3,4,6,7,12,12bβ-octahydro-indolo[2,3-a]quinolizin-1-ol, (−)-1α-isopropyl-1,2,3,4,6,7,12,12bβ-octahydroindolo[2,3-a]quinolizin-1-ol, (+)-1α-isopropyl-1,2,3,4,6,7,12,12bβ-octahydroindolo[2,3-a]quinolizin-1-ol, 1β-Isopropyl-1,2,3,4,6,7,12,12bβ-octahydro-indolo[2,3-a]quinolizine, (1α-Isopropyl-1,2,3,4,6,7,12,12bβ-octahydro-indolo[2,3-a]quinolizin-1yl)-methanol, 1β-n-Propyl-1,2,3,4,6,7,12,12bβ-octahydro-indolo[2,3-a]quinolizin-1yl)-methanol, 2-(1α,2,3,4,6,7,12,12bβ-Octahydro-indolo[2,3-a]quinolizin-1-yl)-butan-2-ol, 1-(1,2α,3,4,6,7,12,12bα-Octahydro-indolo[2,3-a]quinolizin-2-yl)-propan-1-ol, 2-(1α,2,3,4,6,7,12,12bβ-Octahydro-indolo[2,3-a]quinolizin-1-yl)-propan-2-ol, 1-s-Butyt-1,2,3,4,6,7,12,12bβ-octahydroindolo[2,3-a]quinolizin-1-ol, 1-Cyclohexyl-1,2,3,4,6,7,12,12bβ-octahydroindolo[2,3-a]quinolizin-1-ol, 9-Fluoro-1α-isopropyl-1,2,3,4,6,7,12,12bβ-octahydro-indolo[2,3-a]quinolizin-1-ol, (1α-Methyl-1,2,3,4,6,7,12,12bβ-octahydroindolo[2,3-a]quinolizin-1-yl)-methanol, (−)-(1α-Methyl-1,2,3,4,6,7,12,12bβ-octahydroindolo[2,3-a]quinolizin-1-yl)-methanol, (+)-(1α-Methyl-1,2,3,4,6,7,12,12bβ-octahydroindolo[2,3-a]quinolizin-1-yl)-methanol, (1α-Ethyl -1,4,6,7,12,12bβ-hexahydroindolo[2,3-a]quinolizin-1-yl)-methanol, 3β,4α-Dimethyl-1,2,3,4,6,7,12,12bβ-octahydroindolo[2,3-a]quinolizine, (1,2α,3,4,6,7,12,12bα-Octahydroindolo[2,3-a]quinolizin-2-yl)-propan-2-ol, Ethyl-1,2,3,4,6,7,12,12bα-octahydroindolo[2,3-a]quinolizin-2-yl)-methanol, (2a-Ethyl-1,2,3,4,6,7,12,12bβ-octahydroindolo[2,3-a]quinolizin-2-yl)-methanol, (1-αEthyl-1,2,3,4,6,7,12,12bβ-octahydroindolo[2,3-a]quinolizin-1-ylmethoxy)-acetic acid ethyl ester, 1-(2α-ethyl-1,2,3,4,6,7,12,12bα-octahydro-indolo[2,3-a]quinolizin-2-yl)-ethanone, 1-(2α-ethyl-1,2,3,4,6,7,12,12bα-octahydro-indolo[2,3-a]quinolizin-2-yl)-ethanol, 2-(2α-ethyl-1,2,3,4,6,7,12,12bα-octahydro-indolo[2,3-a]quinolizin-2-yl)-propan-2-ol, 2-(3-ethyl-1,2α,3α,4,6,7,12,12bα-octahydro-indolo[2,3-a]quinolizin-2-yl)-propan-2-ol, (3-ethyl-2-methyl-1α,2β,3β,4,6,7,12,12bβ-octahydro-indolo[2,3-a]quinolizin-1-yl)-methanol, 3-ethyl-1,2-dimethyl-1α,2β,3β,4,6,7,12,12bβ-octahydro-indolo[2,3-a]quinolizine, 1,2-dimethyl-1,2,3,4,6,7,12,12bβ-octahydro-indolo[2,3-a]quinolizin-1β-ol, (1-ethyl-2-methyl-1β,2β,3β,4,6,7,12,12bα-octahydro-indolo[2,3-a]quinolizin-3-yl)-methanol, 1-β-Hydroxymethyl-1-methyl-1,2,3,4,6,7,12,12bβ-octahydro-indolo[2,3-a]quinolizine-6β-carboxylic acid methyl ester, 5,6,7,7aβ,8,9,10,11,11αβ,11bα-Decahydro-12-oxa-6a-aza-indeno[1,2-a]fluorene, 2,3,4,4aβ5,6,7,8,13bβ,13cβ-Decahydro-1H-13-oxa-6a-aza-indeno[1,2-c]phenanthrene, 2,3,4,4aβ,5,6,7,8,13bα,13cβ-Decahydro-1H-13-oxa-6a-aza-indeno[1,2-c]phenanthrene, 2,3,4,4aβ,5,6,7,8,13,13bβ-decahdro-1H-6a,13-diaza-indeno[1,2,-c]phenanthren-13cβ-ol,(−)-2,3,4,4aβ,5,6,7,8,13,bβ-decahydro-1H-6a,13-diaza-indeno[1,2-c]phenanthren-13cβ-ol, (+)-2,3,4,4aβ,5,6,7,8,13,13bβ-decahydro-1H-6a,13-diaza-indeno[1,2-c]phenanthrenyl)-13cβ-methanol or 5,6,7,7a,11,11b,12-Decahydro-6a,12-diaza-indeno[1,2-a]fluoren-11a-ol.

The terms employed herein have the following meanings:

The term "halo" or "halogen", as employed herein as such or as part of another group, refers to chlorine, bromine, fluorine or iodine.

The term "carboxyl", as employed herein, refers to a —COOH group.

The term "oxo", as employed herein, refers to an =O group.

The term "$(C_1-C_6)$alkyl", as employed herein as such or as part of another group, refers to a straight or branched carbon chain having 1 to 6 carbon atoms. Representative examples of $(C_1-C_6)$ alkyl include, but are not limited to, methyl, ethyl, n-propyl, isopropyl, n-butyl, isobutyl, sec-butyl, tert-butyl, n-pentyl, isopentyl, neopentyl, n-hexyl, and the like.

The term "$(C_2-C_6)$alkenyl", as employed herein as such or as part of another group, refers to a straight or branched chain radical having 2 to 6 carbon atoms, and containing (a) double bond(s).

The term "$(C_3-C_7)$cycloalkyl", as employed herein as such or as part of another group, refers to a saturated cyclic hydrocarbon group containing 3 to 7 carbons. Representative examples of cycloalkyl include, but are not limited to, cyclopropyl, cyclobutyl, cyclopentyl, cyclohexyl, and the like.

The term "$(C_3-C_7)$cycloalkyl$(C_1-C_6)$alkyl", as employed herein refers to a $(C_3-C_7)$cycloalkyl group, as defined herein, appended to the parent molecular moiety through a $(C_1-C_6)$ alkyl group, as defined herein.

The term "aryl", as employed herein as such or as part of another group, refers to a monocyclic or bicyclic aromatic group containing 6 to 12 carbon atoms. Representative examples of aryl include, but are not limited to, phenyl, naphthyl, and the like.

The term "aryl$(C_1-C_6)$alkyl", as employed herein as such or as part of another group, refers to an aryl group, as defined herein, appended to the parent molecular moiety through an $(C_1-C_6)$alkyl group, as defined herein.

The term "aryloxy", as employed herein as such or as part of another group, refers to an aryl group, as defined herein, appended to the parent molecular moiety through an —O— group.

The term "aryl$(C_1-C_6)$alkoxy", as employed herein as such or as part of another group, refers to an aryl group, as defined herein, appended to the parent molecular moiety through an $(C_1-C_6)$alkoxy group, as defined herein.

The term "aryloxy$(C_1-C_6)$alkyl, as employed herein, refers to an aryloxy group, as defined herein, appended to the parent molecular moiety through an $C_1-C_6$)group, as defined herein.

The term "aryl$(C_1-C_6)$alkyl, as employed herein, refers to an aryl$(C_1-C_6)$alkoxy group, as defined herein, appended to the parent molecular moiety through an $(C_1-C_6)$alkyl group, as defined herein.

The term "hydroxy", as employed herein as such or as part of another group, refers to an —OH group.

The term "hydroxy$(C_1-C_6)$alkyl", as employed herein as such or as part of another group, refers to at least one hydroxy group, as defined herein, appended to the parent molecular moiety through a $(C_1-C_6)$alkyl group, as defined herein. Representative examples of hydroxy$(C_1-C_6)$alkyl include, but are not limited to, hydroxymethyl, 2-hydroxyethyl, 1-hydroxyethyl, 3-hydroxypropyl, 1-hydroxypropyl, 1-methyl-1-hydroxyethyl, 1-methyl-1-hydroxypropyl, and the like.

The term "halo$(C_1-C_6)$alkyl", as employed herein, refers to one or more halogen, as defined herein, appended to the parent molecular moiety through a $(C_1-C_6)$alkyl group, as defined herein. Representative examples of halo$(C_1-C_6)$alkyl include, but are not limited to, fluoromethyl, difluoromethyl, trifluoromethyl, 2-chloroethyl, 3-bromopropyl, and the like.

The term "amino", as employed herein as such or as part of another group, refers to a —NH$_2$ group.

The term "amino$(C_1-C_6)$alkyl", as employed herein, refers to an amino group, as defined herein, appended to the parent molecular moiety through a $(C_1-C_6)$alkyl group, as defined herein. Representative examples of amino$(C_1-C_6)$alkyl include, but are not limited to, aminomethyl, 2-aminoethyl, 1-aminoethyl, 3-aminopropyl, 2-aminopropyl, 4-aminobutyl, 1-methyl-1-aminoethyl, and the like.

The term "mono- or di($C_1$-$C_6$)alkylamino", as employed herein as such or as part of another group, refers to one or two ($C_1$-$C_6$)alkyl group(s), as defined herein, appended to the parent molecular moiety through an amino group, as defined herein. Representative examples of mono- or di($C_1$-$C_6$)alkylamino include, but are not limited to methylaamino, ethylamino, propylamino, butylamino, dimethylamino, diethylamino, N-ethyl-N-methylamino, and the like.

The term "mono- or di($C_1$-$C_6$)alkylamino($C_1$-$C_6$)alkyl", as employed herein, refers to a mono- or di($C_1$-$C_6$)alkylamino group, as defined herein, appended to the parent molecular moiety through a ($C_1$-$C_6$)alkyl group, as defined herein. Representative examples of mono- or di($C_1$-$C_6$)alkylamino($C_1$-$C_6$)alkyl include, but are not limited to, N,N-dimethylaminomethyl, N,N-diethylaminomethyl, N-methylamninoethyl, N-methylaminopropyl, N-ethyl-N-methylaminomethyl, and the like.

The term "($C_1$-$C_6$)alkoxy", as employed herein as such or as part of another group, refers to a ($C_1$-$C_6$)alkyl, as defined herein, appended to the parent molecular moiety through an —O— group. Representative examples of ($C_1$-$C_6$)alkoxy include, but are not limited to, methoxy, ethoxy, propoxy, butoxy, isobutoxy, sec-butoxy, tert-butoxy, and the like.

The term "($C_1$-$C_6$)alkoxy($C_1$-$C_6$)alkyl", as employed herein as such or as part of another group, refers to at least one ($C_1$-$C_6$)alkoxy group, as defined herein, appended to the parent molecular moiety through an ($C_1$-$C_6$)alkyl group, as defined herein. Representative examples of ($C_1$-$C_6$)alkoxy ($C_1$-$C_6$)alkyl include, but are not limited to mnethoxymethyl, ethoxymethyl, 2-methoxyethyl, 2-ethoxyethyl, 3,3-dimethoxypropyl, 2,4-dimethoxybutyl and the like.

The term "hydroxy($C_1$-$C_6$)alkoxy", as employed herein as such or as part of another group, refers to a hydroxy group, as defined herein, appended to the parent molecular moiety through an ($C_1$-C6)alkoxy group, as defined herein.

The term "hydroxy($C_1$-$C_6$)alkoxy($C_1$-$C_6$)alkyl, as employed herein, refers to a hydroxy($C_1$-$C_6$)alkoxy group, as defined herein, appended to the parent molecular moiety through an ($C_1$-$C_6$)alkyl group, as defined herein.

The term "carbamoyl", as employed herein as such or as part of another group, refers to a —$CONH_2$ group.

The term "mono- or di($C_1$-$C_6$)-alkylcarbamoyl", as employed herein, refers to one or two ($C_1$-$C_6$)alkyl group(s), as defined herein, appended to the parent molecular moiety through a —HNCO— or —NCO— group. Representative examples of mono- or di($C_1$-$C_6$)-alkylcarbamoyl include, but are not limited to N-methylcarbamoyl, N-ethylcarbamoyl, N-propylcarbamoyl, N,N-dimethylcarbamoyl, N,N-diethylcarbamoyl and the like.

The compounds of formula I and IA, IB, IC, ID and IE, as well as the pharmaceutically acceptable salts and esters thereof, are referred to below as the compounds of the invention, unless otherwise indicated.

The invention includes within its scope all the possible stereoisomers of the compounds, including geometric isomers, e.g. Z and E isomers (cis and trans isomers), and optical isomers, e.g. diastereomers and enantiomers. Furthermore, the invention includes in its scope both the individual isomers and any mixtures thereof, e.g. racemic mixtures. The individual isomers may be obtained using the corresponding isomeric forms of the starting material or they may be separated after the preparation of the end compound according to conventional separation methods. For the separation of optical isomers, e.g. enantiomers, from the mixture thereof the conventional resolution methods, e.g. fractional crystallisation, may be used.

Pharmaceutically acceptable salts, e.g. acid addition salts with both organic and inorganic acids are well known in the field of pharmaceuticals. Non-limiting examples of these salts include chlorides, bromides, sulfates, nitrates, phosphates, sulfonates, formates, tartrates, maleates, citrates, benzoates, salicylates and ascorbates. Pharmaceutically acceptable esters, when applicable, may be prepared by known methods using pharmaceutically acceptable acids that are conventional in the field of pharmaceuticals and that retain the pharmacological properties of the free form. Non-limiting examples of those esters include esters of aliphatic or aromatic alcohols, e.g. methyl, ethyl, propyl, isopropyl, butyl, isobutyl, sec-butyl and tert-butyl esters.

The compounds of the invention can be prepared analogously or according to the methods known in the literature using suitable starting materials. The starting materials of formulae II, m and IV are commercially available or can be prepared via a variety of known svnth-etic routes known in the literature.

For example, the starting materials used are arylalkylamines of formula (II)

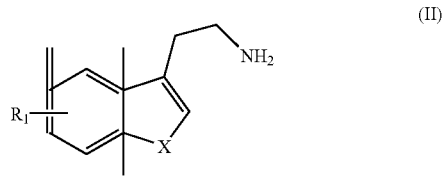

(II)

wherein R1 is as defined above and X is NH, O, CH2 or S.

When X is O, the amines of formula (II) can be prepared, for example, according to the process disclosed in the U.S. Pat. No. 4,710,504. When X is $CH_2$, the compounds of formula (II) can be prepared as described in *J. Med. Chem.* 10 (1967) 856-859. When X is S, the compounds of formula (II) can be prepared by decarboxylation of the corresponding 3-(thianaphten-3-yl)-L-alanine.

Other starting materials used are compounds of formula (III)

(III)

wherein $R_3$ is as defined above and $R_{11}$ is OH or halogen.

Furthermore, the starting materials used are compounds of formula (IV)

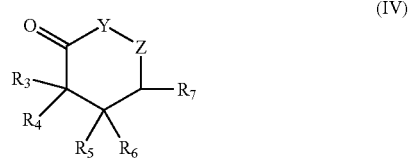

(IV)

wherein $R_3$-$R_7$ and Z are as defined above and Y is O or NH. Compounds of formula (IV) can be prepared according to the methods described in *Tetrahedron* 33 (1977) 1803-1808. Analogously, the corresponding acid chlorides can be used instead of lactones (Y=O). When $R_3$ and $R_5$ form a ring, compounds of formula (IV) are obtained by the partial reduction of their corresponding anhydrides.

In general, the compounds of formula (I), wherein X is NH, O or S, can be prepared e.g. analogously or according to the following reaction scheme 1:

Scheme 1

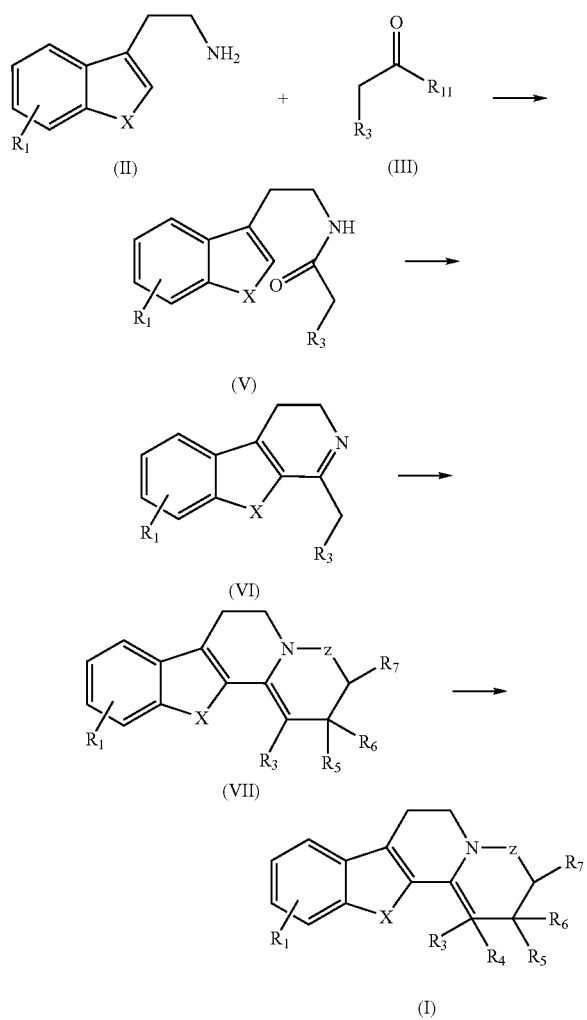

wherein $R_1$, $R_3$-$R_7$ and Z are as defined above.

According to the reaction route of scheme I, alkylation of amines (II) with compounds of formula (III) gives amides (V) which are converted into enamines (VII) via beta carbolines (V) by Bischler-Napieralski reaction followed by ring D formation by allowing compounds of formula (VI) to react with 1,3-dihaloalkanes under basic conditions as described in *Gazz. Chim. Ital.* 111 (1981) 257-267. In the last step, compounds of formula (I) are obtained 1) by oxidation of enamines (VII) using potassium iodide, iodide and air or 2) by reaction of enamines (VII) with formaldehyde in presence of Hünig base at 60° C.

Another route for preparing compounds of formula (I), wherein X is $NR_2$, O, $CH_2$ or S, is illustrated in scheme 2

Scheme 2

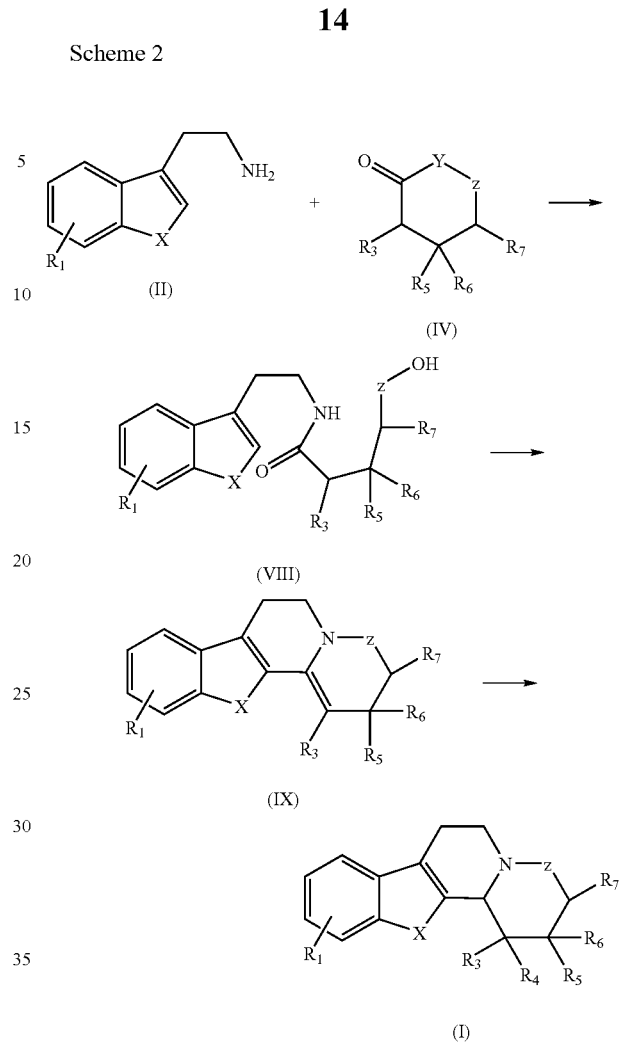

wherein X is $NR_2$, O, $CH_2$ or S, $R_1$-$R_7$ and Z are as defined above.

In scheme 2 arylalkylamines of formula (II), wherein X is NH, O, $CH_2$, or S, are reacted with compounds of formula (IV), or the corresponding acid chloride, to give amides (VIII) as described in *Tetrahedron* 33 (1977) 1803-1808. The Bischler-Napieralski cyclization of the intermediates (VI) leads to enamines (IX) which are converted into compounds of formula (I).

The compounds of formula (I), wherein X is NH, can be alkylated with alkylhalides in the presence of a suitable base at room temperature (*Heterocycles* 27 (1988) 1179-1190) according to following scheme 3:

Scheme 3

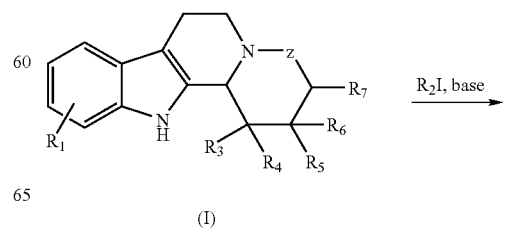

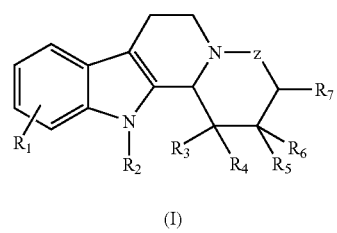

(I)

wherein $R_1$-$R_7$ and Z are as defined above.

A further method for preparing compounds of formula (I) is illustrated in scheme 4:

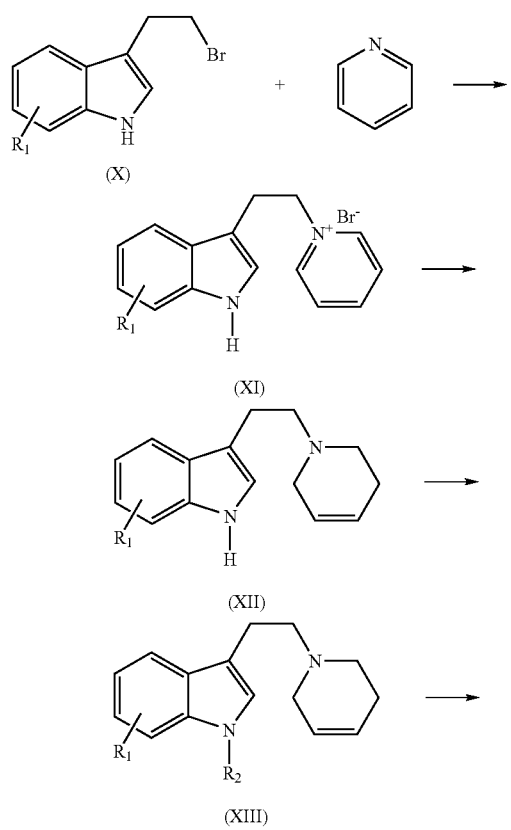

wherein $R_2$ is BOC and $R_1$, $R_5$ and $R_6$ are as defined above.

In scheme 4 pyridine is alkylated with tryptophyl bromides (X) to give pyridinium salts (XI) whose partial reduction gives compounds of formula (XII). Protection of compounds of formula (XII) using di-t-butyl dicarbonate under basic conditions gives compounds of formula (XIII). The Polonovski-Potier reaction of the obtained intermediates and their cyclisation using MeOH/HCl yield the compounds of formula (I).

A further process for the preparation of compounds of formula (I), wherein X is O, S or NH, $R_1$ and $R_3$-$R_8$ are as defined above, is shown in the following scheme 5:

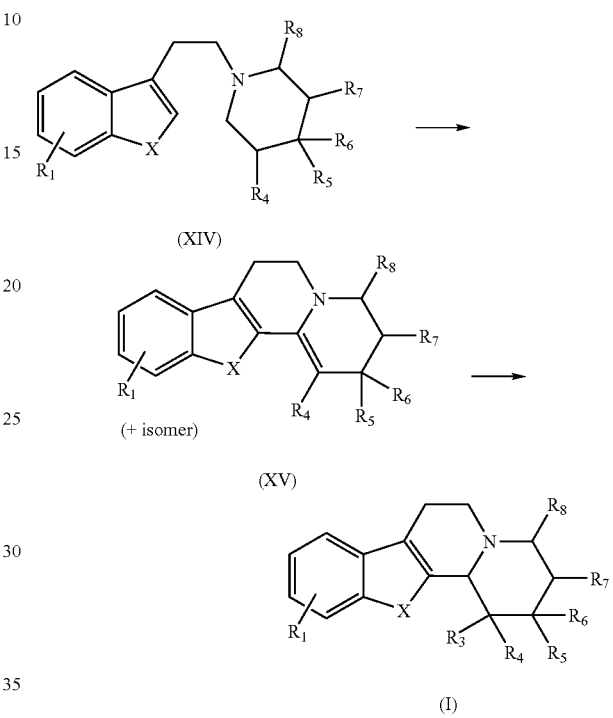

In scheme 5 oxidative cyclization of derivative (XIV) with mercuric acetate according to the method described in *Heterocycles* 32 (1991) 489-497 gives enamine (XV). This intermediate can be oxidized or treated with formaldehyde as in scheme 1 or reduced with sodium borohydride to give compounds of formula (I).

A further method for preparing compounds of formula (I), wherein $R_6$ and $R_7$ form a bond, is illustrated in scheme 6:

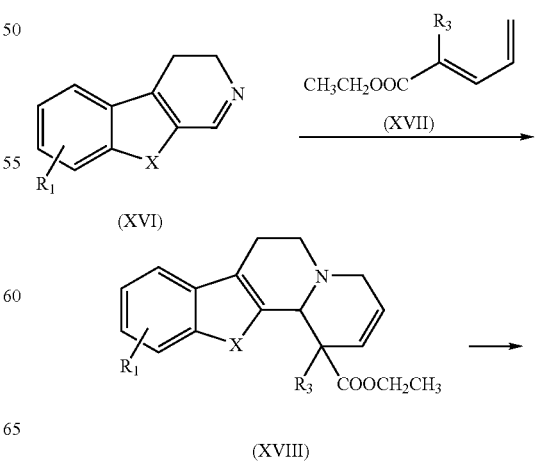

-continued

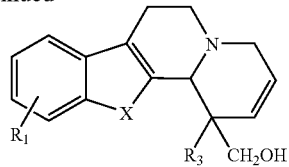

(I)

wherein X is NH and R$_3$ is lower alkyl.

Applying the method described in *J. Org. Chem.* 52 (1987) 353-356, the hetero-Diels-Alder reaction of 3,4-dihydro-β-carboline (XVI) with diene ester (XVII), prepared by the Wittig reaction as described in *Can. J Chem.* 65 (1987) 670-682, gives compounds of formula (XVII), which are then reduced to alcohols of formula (I).

A further method for preparing compounds of formula (I) is illustrated in scheme 7.

Scheme 7

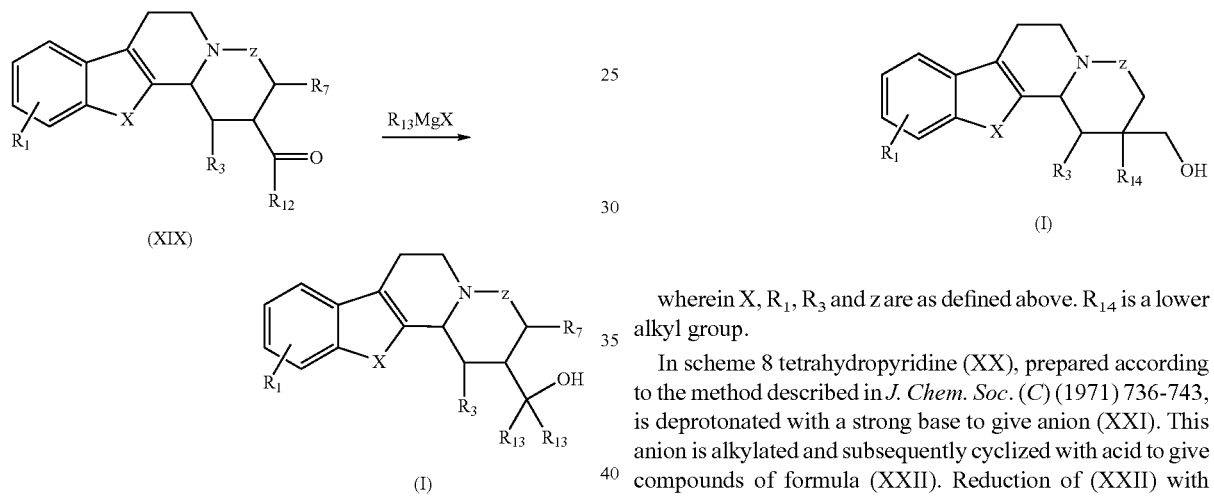

wherein X, R$_1$, R$_3$, R$_7$ and z are as defined above. R$_{12}$ can be H or OCH$_3$ and R$_{13}$ can be an alkyl or aryl group.

In scheme 7, compounds of formula (XIX), when R$_{12}$ is H, are prepared as described in *J Chem. Soc., Chem. Commun.* (1995) 2317-2318, and compounds of formula (XIX), when R$_{12}$ is OCH$_3$, are prepared as described in *J. Chem. Soc. (C)* (1971) 736-743. Compounds of formula (XIX) are reacted with Grignard reagents to give compounds of formula (I). When R$_{12}$ in formula (XIX) is H, the other R$_{13}$ group in formula (I) is also H.

A new method to prepare certain compounds of formula (I) is shown in scheme 8.

Scheme 8

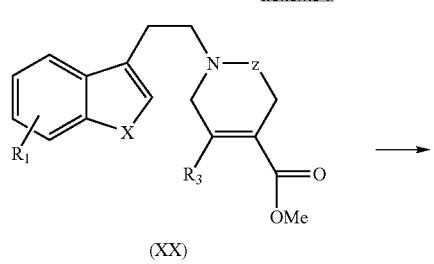

(XX)

-continued

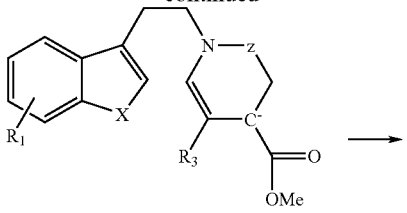

(XXI)

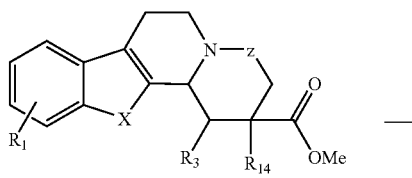

(XXII)

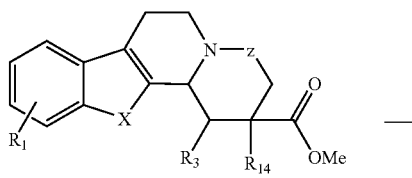

(I)

wherein X, R$_1$, R$_3$ and z are as defined above. R$_{14}$ is a lower alkyl group.

In scheme 8 tetrahydropyridine (XX), prepared according to the method described in *J. Chem. Soc. (C)* (1971) 736-743, is deprotonated with a strong base to give anion (XXI). This anion is alkylated and subsequently cyclized with acid to give compounds of formula (XXII). Reduction of (XXII) with LiAlH$_4$ then affords compounds of formula (I).

The resolution of the racemic compounds of formula (I) can be performed, for example, by converting compounds of formula (I) into their diastereoisomers salt mixture by reaction with an optically active acid such as D-tartaric acid, dibenzoyl-D-tartaric acid, etc and by separation of the diastereoisomers by crystallization.

It is obvious to a skilled person that, in the above reactions, any starting material or intermediate can be protected, if necessary, in manner well known in the chemical field. Any protected functionality is subsequently deprotected in a usual manner.

It should be noted that the above described synthetic routes are meant to illustrate the preparation of the compounds of the invention and the preparation is by no means limited thereto, i.e. other synthetic methods which are within the general knowledge of a skilled person are also possible.

The compounds of the invention may be converted, if desired, into their pharmaceutically acceptable salt or ester form using methods well known in the art.

The present invention will be explained in more detail by the following examples. The examples are meant only for illustrating purposes and do not limit the scope of the invention defined in claims.

EXAMPLE 1

1-Propyl-4,9-dihydro-3H-β-carboline 8.00 g (50.0 mmol) of tryptamine was dissolved in 150 ml of ethyl acetate and 4.80 ml (52.0 mmol) of n-butyric acid was slowly added. After standing for 4 h at 0° C., the reaction mixture was filtered to give 12.30 g (49.5 mmol) of tryptamine butyrate, which was melted. The melt was heated at 200° C. and kept for 30 min at that temperature. Water formed was removed using a Dean-Stark apparatus. The melt after cooling was mixed with 120 ml of toluene, 23.5 ml (257.7 mmol) of freshly distilled phosphorus oxychloride was added and the reaction mixture was refluxed for 4 h. The solution was evaporated in vacuum and the dark oil was mixed with 20% solution of acetic acid (3×50 ml). The solid was filtered off and the aqueous solution was made alkaline with 25% ammonium hydroxide under cooling and extracted with dichloromethane (3×50 ml). The combined organic phases were dried over sodium sulfate, the drying agent was filtered off and the filtrate was evaporated to give the title compound, which was purified by column chromatography (silica gel, dichloromethane/methanol, 95:5).

NMR: 1.00 (t, 3H), 1.75 (m, 2H), 2.66 (t, 2H), 2.87 (t, 2H), 3.90 (t, 2H), 7.00-7.62 (m, 4H), 8.94 (br s, 1H). MS: 212 (28%), 211 (12%), 197 (25%), 184 (100%), 169 (13%).

EXAMPLE 2

1-Isobutyl-4,9-dihydro-3H-β-carboline

The procedure of example 1 was repeated, except that isovaleric acid was used instead of n-butyric acid.

NMR: 0.98 (d, 6H), 2.16 (m, 1H), 2.54 (d, 2H), 2.86 (t, 2H), 3.89 (t, 2H), 7.00-7.62 (m, 4H), 8.60 (br s, 1H). MS: 226 (16%), 211 (18%), 184 (100%), 169 (13%).

EXAMPLE 3

1-Butyl-4,9-dihydro-3H-β-carboline

The procedure of example 1 was repeated, except that n-valeric acid was used instead of n-butyric acid.

NMR: 1.00 (t, 3H), 7.00-7.62 (m, 4H), 8.64 (br s, 1H). MS: 226 (18%), 211 (18%), 184 (100%), 169 (14%).

EXAMPLE 4

1-(2-Methyl-butyl)-4,9-dihydro-3H-β-carboline

The procedure of example 1 was repeated, except that 3-methylvaleric acid was used instead of n-butyric acid.

NMR: 0.84 (t, 3H), 0.87 (d, 3H), 7.05-7.60 (m, 4H), 12.2 (br s, 1H). MS: 240 (9%), 225 (10%), 211 (10%), 185 (13%), 184 (100%), 183 (14%), 155 (24%).

EXAMPLE 5

1-Cyclohexylmethyl-4,9-dihydro-3H-β-carboline

The procedure of example 1 was repeated, except that cyclohexylacetic acid was used instead of n-butyric acid.

NMR: 1.0-1.9 (m, 11H), 2.56 (d, 2H), 2.85 (m, 2H), 3.88 (m, 2H), 7.14-7.63 (m, 4H), 8.55 (br s, 1H). MS: 266 (8%), 185 (15%), 184 (100%), 183 (12%), 155 (17%).

EXAMPLE 6

1,β-Isopropyl-1,2,3,4,6,7,12,12bβ-octahydroindolo[2,3-a]quinolizine 2.56 g (11.5 mmol) of 4,9-Dihydro-1-isobutyl-3-H-pyrido[3,4-b]indole (example 2), 2 ml of N-ethyldiisopropylamine, and 1.35 ml (13.8 mmol) of 1-bromo-3-chloropropane were dissolved in 50 ml of acetonitrile. The mixture was refluxed under argon for 8 h. After evaporation of the solvent, 20 ml of methanol and 1.3 g (34.5 mmol) of sodium borohydride were added. The reaction mixture was stirred for 1 h at room temperature and 20 ml of water was then added. The reaction mixture was extracted with dichloromethane (3×50 ml). The combined organic phases were dried over sodium sulfate, the drying agent was filtered off and the filtrate was evaporated to give the title compound, which was purified by column chromatography (silica gel, dichloromethane/methanol, 95:5).

NMR: 1.02 (br s, 6H), 7.11 (t, 1H), 7.18 (t, 1H), 7.35 (d, 1H), 7.48 (d, 1H), 7.85 (br s, 1H). MS: 267 (100%), 253 (20%), 197 (35%), 170 (30%), 169 (30%).

EXAMPLE 7

2-(1α,2,3,4,6,7,12,12bβ-Octahydroindolo[2,3-a]quinolizin-1-yl)-butan-2-ol

To a solution of 190 mg (0.7 mmol) of 1-(1,2,3,4,6,7,12,12b-octahydro-indolo[2,3-a]quinolizin-1-yl)-ethanone (*Tetrahedron Lett.* 30 (1989) 719-722) in 5 ml of dichloromethane at −60° C. was added 0.11 ml (0.8 mmol) of ethylmagnesium bromide (1.0 M). The reaction mixture was stirred 30 min at that temperature and 2 h at room temperature. Water (10 ml) was then added and the reaction mixture was extracted with dichloromethane (3×50 ml). The combined organic phases were dried over sodium sulfate, the drying agent was filtered off and the filtrate was evaporated to give the title compound, which was purified by column chromatography (silica gel, dichloromethane/methanol, 95:5).

NMR: 0.97 (t, 3H), 1.30 (s, 3H), 4.69 (br s, 1H), 7.00-7.50 (m, 4H), 8.36 (br s, 1H). MS: 297 (100%), 281 (30%), 269 (35%), 225 (28%), 197 (45%), 170 (35%), 169 (34%).

EXAMPLE 8

2-(1α,2,3,4,6,7,12,12bβ-Octahydroindolo[2,3-a]quinolizin-1-yl)-propan-2-ol

The procedure of example 7 was repeated, except that methylmagnesium bromide (excess) was used instead of ethylmagnesium bromide.

NMR: 1.37 (s, 3H), 1.42 (s, 3H), 4.73 (br s, 1H), 7.00-7.50 (m, 4H), 8.18 (br s, 1H). MS: 283 (100%), 267 (42%), 225 (33%), 197 (60%), 170 (50%), 169 (50%).

EXAMPLE 9

1α-Isopropyl-1,2,3,4,6,7,12,12bβ-octahydroindolo[2,3-a]quinolizin-1-ol (Compound A)

5.13 g (23.0 mmol) of 4,9-Dihydro-1-isobutyl-3-H-pyrido[3,4-b]indole, 4 ml of N-ethyldiisopropylamine, and 2.7 ml (27.6 mmol) of 1-bromo-3-chloropropane were dissolved in 100 ml of acetonitrile. The mixture was refluxed under argon for 8 h. The dark solution was concentrated to an oil, which was treated with 20% sodium hydroxide. After 10 min stirring, the solution was extracted with dichloromethane (3×50 ml). The combined organic phases were dried over sodium sulfate, the drying agent was filtered off and the filtrate was evaporated to give the corresponding enamine, which was dissolved in 100 ml of acetonitrile. 7.0 g (27.6 mmol) of iodine and 4.6 g (27.6 mmol) of potassium iodide were added. The reaction mixture was stirred in the dark under air for 3 h. After evaporation of the solvent, 50 ml of methanol and, with cooling, 2.6 g (69 mmol) of sodium borohydride were added. The reaction mixture was stirred for 1 h at room temperature and 20 ml of water was then added. The reaction mixture was extracted with dichloromethane (3×50 ml). The combined organic phases were dried over sodium sulfate, the drying agent was filtered off and the filtrate was evaporated to give the title compound, which was purified by column chromatography (silica gel, dichloromethanetmethanol, 95:5).

NMR: 0.47 (d, 3H), 0.90 (d, 3H), 3.48 (br s, 1H), 7.00-7.50 (m, 4E), 8.92 (br s, 1H). MS: 284 (14%), 239 (13%), 171 (100%), 170 (16%), 169 (33%).

EXAMPLE 10

1α-Ethyl-2α-methyl-1,2,3,4,6,7,12,12bβ-octahydro-indolo[2,3-a]quinoulzin-1-ol (Compound B)

The procedure of example 9 was repeated, except that 4,9-dihydro-1-propyl-3-H-pyrido[3,4-b]indole was used instead of 4,9-dihydro-1-isobutyl-3-H-pyrido[3,4-b]indole and 1,3-dibromobutane was used instead of 1-bromo-3-chloropropane.

NMR: 0.69 (t, 3H), 1.00 (d, 3H), 3.20 (br s, 1H), 7.00-7.60 (m, 4H), 9.04 (br s, 1H). MS: 284 (5%), 267 (15%), 225 (100%), 210 (15%), 195 (15%), 182 (72%), 171 (41%), 170 (22%), 169 (32%).

EXAMPLE 11

9-Fluoro-1α-isopropyl-1,2,3,4,6,7,12,12bβ-octahydro-indolo[2,3-a]quinolizin-1-ol The procedure of example 9 was repeated, except that 6-fluoro-1-isobutyl-4,9-dihydro-3H-pyrido[3,4-b]indole (prepared from 5-fluorotryptamine as described in example 2) was used instead 4,9-dihydro-1-isobutyl-3H-pyrido[3,4-b]indole.

NMR: 0.45 (d, 3H), 0.89 (d, 3H), 3.32 (s, 1H), 6.8-7.25 (m, 3H), 8.94 (br s, 1H). MS: 302 (26%), 203 (13%), 189 (100%), 161 (26%).

EXAMPLE 12

1-s-Butyl-1,2,3,4,6,7,12,12bβ-octahydro-indolo[2,3-a]quinolizin-1-ol (mixture of isomers) (Compound C)

The procedure of example 9 was repeated, except that 1-(2-methylbutyl)-4,9-dihydro-3H-pyrido[3,4-b]indole was used instead of 4,9-dihydro-1-isobutyl-3H-pyrido[3,4-b]indole.

NMR: 0.48 (d, 3H, major isomer), 0.69 (t, 3H, minor isomer), 0.82 (t, 3H, major isomer), 0.92 (d, 3H, minor isomer), 3.30 (s, 1H), 7.0-7.5 (m, 4H), 8.88 (br s, 1H, minor isomer), 8.93 (br s, 1H, major isomer). MS: 298 (23%), 172 (24%), 171 (100%), 170 (15%), 169 (23%), 143 (29%).

EXAMPLE 13

1-Cyclohexyl-1,2,3,4,6,7,12,12bβ-octahydro-indolo[2,3-a]quinolizin-1-ol

The procedure of example 9 was repeated, except that 1-cyclohexylmethyl-4,9-dihydro-3H-pyrido[3,4-b]indole was used instead 4,9-dihydro-1-isobutyl-3H-pyrido[3,4-b]indole.

NMR: 3.35 (br s, 1H), 7.02-7.55 (m, 4H), 8.98 (br s, 1H). MS: 324 (21%), 172 (12%), 171 (100%), 170 (10%), 169 (15%), 143 (22%).

EXAMPLE 14

(1α-Isopropyl-1,2,3,4,6,7,12,12bβ-octahydro-indolo[2,3-a]quinolizin-1-yl)-methanol The procedure of example 9 was repeated, except that instead of oxidation using iodine and potassium iodide, the enamine obtained was treated with 40% aqueous formaldehyde and the reaction mixture was heated to reflux for 3 h and the solvent was evaporated. The residue was diluted with ethyl acetate and washed with brine. The organic phase was dried over sodium sulfate, the drying agent was filtered off and the filtrate was evaporated to give the title compound, which was purified by column chromatography (silica gel, dichloromethane/methanol, 98:2).

NMR: 0.58 (br s, 3H), 0.82 (d, 3H), 3.07 (br s, 1H), 3.62 (d, 1H), 4.13 (d, 1H), 7.00-7.50 (m, 4H), 9.41 (br s, 1H). MS: 298 (100%), 297 (55%), 281 (60%), 170 (75%), 169 (52%).

EXAMPLE 15

(1α-n-Propyl-1,2,3,4,6,7,12,12bβ-octahydroindolo[2,3-a]quinolizin-1-yl)-methanol The procedure of example 14 was repeated, except that 4,9-dihydro-1-butyl-3-H-pyrido[3,4-b]indole was used instead of 4,9-dihydro-1-isobutyl-3-H-pyrido[3,4-b]indole.

NMR: 0.81 (t, 3H), 3.34 (br s, 1H), 3.65 (d, 1H), 3.82 (d, 1H), 7.00-7.50 (m, 4H), 10.07 (br s, 1H). MS: 298 (100%), 297 (65%), 281 (67%), 170 (75%), 169 (52%).

EXAMPLE 16

(1α-Methyl-1,2,3,4,6,7,12,12bβ-octahydroindolo[2,3-a]quinolizin-1-yl)-methanol

The procedure of example 14 was repeated, except that 1-ethyl-4,9-dihydro-3H-pyrido[3,4-b]indole was used instead 4,9-dihydro-1-isobutyl-3H-pyrido[3,4-b]indole.

NMR: 0.91 (s, 3H), 3.37 (br s, 1H), 3.70 (d, 1H), 3.76 (d, 1H), 7.0-7.6 (m, 4H), 9.78 (br s, 1H). MS: 270 (97%), 269 (100%), 253 (53%), 197 (48%), 170 (68%), 169 (62%).

EXAMPLE 17

(1α-Ethyl-1,4,6,7,12,12bβ-hexahydroindolo[2,3-a]quinolizin-1-yl)-methanol

A mixture of 0.34 g (2.0 mmol) of 3,4-dihydro-β-carboline and 0.39 g (2.5 mmol) of ethyl 2-ethylpenta-2,4-dienoate in 5 ml of chlorobenzene was refluxed for 16 h. The solvent was evaporated and the residue was subjected to column chromatography (silica gel, dichloromethane/methanol, 99:1) to give the ester intermediate. This product was reduced in the usual manner with lithium aluminum hydride in dry tetrahydrofuran to afford the title compound.

NMR: 0.82 (t, 3H), 3.69 (d, 1H), 3.70 (br s, 1H), 3.90 (d, 1H), 5.42 (ddd, 1H), 5.97 (ddd, 1H), 7.0-7.5 (m, 4H), 10.02 (br s, 1H). MS: 282 (31%), 171 (14%), 170 (100%), 169 (52%).

EXAMPLE 18

2β-Methoxy-1,2,3,4,6,7,12,12bα-octahydro-indolo[2,3-a]quinolizine and

2α-Methoxy-1,2,3,4,6,7,12,12bα-octahydro-indolo[2,3-a]quinolizine (Compound D)

1.16 g (14.7 mmol) of pyridine and 3.0 g (13.4 mmol) of tryptophyl bromide were dissolved in 15 ml of dry diethyl ether. The reaction mixture was heated with stirring at 60° C. until complete evaporation of the solvent. The mixture was then heated at 100° C. for 2 h to give the corresponding pyridinium bromide salt. This was dissolved in 100 ml of methanol and 1.52 g (40.1 mmol) of sodium borohydride was added in portions with cooling. The reaction mixture was stirred at room temperature for 4 h, followed by addition of 20 ml of water. The reaction mixture was extracted with dichloromethane (3×30 ml). The combined organic phases were dried over sodium sulfate, the drying agent was filtered off and the filtrate was evaporated. The residue was dissolved in 100 ml of dry dichloromethane and 2.91 g (13.3 mmol) of di-t-butyl dicarbonate and 0.149 g (1.2 mmol) of 4-(dimethylamino)pyridine were added. The reaction mixture was stirred for 2 h at room temperature under argon. The solvent was evaporated and the residue purified by colurnn chromatography (silica gel, dichloromethane/methanol, 98:2). The obtained viscous oil was dissolved in 40 ml of dichloromethane and 2.54 g (13.3 mmol) of mCPBA was added. The solution was stirred for 2 h at 0° C., after which the solvent was evaporated and the crude product was purified by column chromatography (silica gel, dichloromethane/methanol, 98:2) to yield the Boc $N_b$-oxide.

To a stirred solution of 0.59 g (1.7 mmol) of Boc $N_b$-oxide in 15 ml of dichloromethane at 0° C. was slowly added 3.0 ml of trifluoroacetic anhydride. The cooling bath was removed and stirring was continued for 2 h at rt, after which the solvent was evaporated. Methanol saturated with hydrogen chloride gas (20 ml) was added and the mixture was refluxed for 2 h. Alkaline work-up and purification by column chromatography (silica gel, dichloromethane/methanol, 98:2) yielded two ethers.

2β-Methoxy-1,2,3,4,6,7,12,12bα-octahydro-indolo[2,3-a]quinolizine:
NMR: 1.54 (ddd, 1H), 3.24 (dd, 1H), 3.38 (dddd, 1H), 3.43 (s, 3H), 7.00-7.50 (m, 4H), 7.77 (br s, 1H). MS: 256 (100%), 255 (86%), 255 (59%), 197 (35%), 169 (30%).

2α-Methoxy-1,2,3,4,6,7,12,12bα-octahydro-indolo[2,3-a]quinolizine:
NMR: 3.41 (s, 3H), 3.67 (br s, 1H), 3.68 (br d, 1H), 7.00-7.50 (m, 4H), 7.72 (br s, 1H). MS: 256 (100%), 255 (75%), 255 (70%), 223 (45%), 197 (40%), 170 (45%), 169 (65%).

EXAMPLE 19

1-(1,2α,3,4,6,7,12,12bα-Octahydroindolo[2,3-a]quinolizin-2-yl)-propan-1-ol

To a solution of 0.086 g (0.3 mmol) of 1,2,3,4,6,7,12,12b-octahydro-indolo[2,3-a]quinolizine-2-carbaldehyde (*J Chem. Soc. Chem. Commun.* 22 (1995) 2317-2318) in 2 ml of dichloromethane at −60° C. was added 0.22 ml (1.7 mmol) of 1M ethylmagnesium bromide. The reaction mixture was stirred for 4 h under argon. Work-up with aqueous sodium hydroxide, followed by extraction with dichloromethane, and purification by column chromatography (silica gel, dichloromethane/methanol, 98:2) gave the title compound.

NMR: 1.02 (t, 3H), 1.93 (br d, 1H), 2.30 (br d, 1H), 6.80-7.40 (m, 4H). MS: 284 (95%), 283 (100%), 225 (80%), 169 (36%).

EXAMPLE 20

(1,2α,3,4,6,7,12,12bα-Octahydroindolo[2,3-a]quinolizin-2-yl)-propan-2-ol

To a solution of 88 mg (0.31 mmol) of 1,2α,3,4,6,7,12,12bα-octahydroindolo[2,3-a]-quinolizine-2-carboxylic acid methyl ester in 3 ml of dry tetrahydrofuran was added dropwise 1 ml (3.0 mmol) of a solution of methylmagnesium chloride (3 M in tetrahydrofuran). The resulting solution was then refluxed for 90 min. The mixture was then worked-up as in example 7 to give the crude alcohol, which was purified by column chromatography (silica gel, dichloromethane/methanol, 95:5) to give the title compound.

NMR: 1.20 (s, 3H), 1.25 (s, 3H), 3.28 (br d, 1H), 7.0-7.5 (m, 4H). MS: 284 (86%), 283 (65%), 225 (100%).

EXAMPLE 21

(1,2α,3,4,6,7,12,12bβ-Octahydroindolo[2,3-a]quinolizin-2-yl)-propan-2-ol

As in example 20, 64 mg (0.23 mmol) of 1,2α,3,4,6,7,12,12bβ-octahydroindolo[2,3-a]-quinolizine-2-carboxylic acid methyl ester in 3 ml of dry tetrahydrofuran and 0.7 ml (2.1 mmol) of a solution of methylmagnesium chloride (3M in tetrahydrofuran) were refluxed for 90 min. Work-up as above gave, after column chromatography (silica gel, dichloromethane/methanol, 90: 10), the title compound.

NMR: 1.17 (s, 3H), 1.18 (s, 3H), 4.57 (br s, 1H), 7.0-7.5 (m, 4H), 8.65 (br s, 1H). MS: 284 (58%), 283 (53%), 225 (100%).

EXAMPLE 22

(2α-Ethyl-1,2,3,4,6,7,12,12bα-octahydroindolo[2,3-a]quinoilzin-2-yl)-methanol

To a stirred solution of 0.36 g (3.6 mmol) of diisopropylamine in 4 m1l of dry tetrahydrofuran at −50° C. was added 2.0 ml (3.6 mmol) of n-butyllithium (1.8 M in hexanes). The mixture was allowed to warm up to −30° C. (15 min), after which it was cooled to −70° C. At this temperature, 0.64 g (3.6 mmol) of hexamethylphosphoramide was added. Stirring was continued for 30 min at this temperature, after which 0.42 g (1.48 mmol) of methyl 1-[2-(3-indolyl)ethyl]-1,2,5,6-tetrahydropyridine4-carboxylate in 7 ml of tetrahydrofuran was added. After stirring for 20 min at −70° C., the mixture was allowed to warm up to −40° C. (15 min). At this temperature, 0.3 g (3.6 mmol) of ethyl iodide was added and stirring was continued for 1 h. The cooling bath was then removed and, after additional 15 min, the mixture was quenched with 5% ammonia. The aqueous layer was extracted with dichloromethane (3×20 ml) and the combined organic layers were washed with water. Drying over sodium sulfate, filtration and evaporation of the solvent gave the crude enamine, which was dissolved in 50 ml of methanol saturated with hydrogen chloride and the resulting solution was stirred for 16 h at room temperature. The solvent was evaporated and the residue was treated with aqueous sodium hydrogen carbonate. After normal extraction procedures (dichloromethane), the solvent was evaporated to give the crude product, which was subjected to column chromatography (silica gel, dichloromethane/methanol, 98:2) to afford the intermediate ester, 2α-ethyl-1,2,3,4,6,7,12,12bα-octahydroindolo[2,3-a]quinolizine-2-carboxylic acid methyl ester. This compound was then treated with lithium aluminum hydride in dry tetrahydrofuran in the usual manner to give, after column chromatography (silica gel, dichloromethane/methanol, 95:5), the title alcohol.

NMR: 0.90 (t, 3H), 3.29 (d, 1H), 3.43 (d, 1H), 3.52 (br d, 1H), 7.0-7.5 (m, 4H). MS: 284 (100%), 283 (98%), 253 (33%), 197 (37%), 170 (33%), 169 (40%), 156 (34%).

EXAMPLE 23

(2α-Ethyl-1,2,3,4,6,7,12,12bβ-octahydroindolo[2,3-a]quinolizin-2-yl)-methanol

A solution of 51 mg (0.16 mmol) of the ester intermediate obtained in example 22 (2α-ethyl-1,2,3,4,6,7,12,12bα-octahydroindolo[2,3-a]quinolizine-2-carboxylic acid methyl ester) in 4 ml of trifluoroacetic acid was refluxed under argon for 16 h. The acid was evaporated and the residue treated with aqueous sodium hydrogen carbonate. After normal extraction procedures (dichloromethane) a crude mixture (20:80) of the two diastereomers, 2α-ethyl-1,2,3,4,6,7,12,12bα-octahydroindolo[2,3-a]quinolizine-2-carboxylic acid methyl ester and 2α-ethyl-1,2,3,4,6,7,12,12bβ-octahydroindolo[2,3-a]quinolizine-2-carboxylic acid methyl ester, was obtained. The latter isomer was separated by column chromatography (silica gel, dichloromethane/methanol, 99:1) and it was then reduced in the usual way with lithium aluminum hydride in dry tetrahydrofuran. Purification as above then gave the title alcohol.

NMR: 0.87 (t, 3H), 3.51 (d, 1H), 3.78 (d, 1H), 7.0-7.5 (m, 4H). MS: 284 (95%), 283 (100%), 253 (30%), 197 (30%), 170 (17%), 169 (23%), 156 (19%).

EXAMPLE 24

1-(2α-Ethyl-1,2,3,4,6,7,12,12bα-octahydroindolo[2,3-a]quinolizin-2-yl)-ethanone and 2-(2α-Ethyl-1,2,3,4,6,7,12,12bα-octahydroindolo[2,3-a]quinolizin-2-yl)-propan-2-ol As in example 20, 230 mg (0.74 imnol) of the ester intermediate obtained in example 22 (2α-ethyl-1,2,3,4,6,7,12,12bα-octahydroindolo[2,3-a]quinolizine-2-carboxylic acid methyl ester) in dry tetrahydrofuran (9 ml) and 3.7 ml (11.1 mmol) of methylmagnesium chloride (3M in tetrahydrofuran) were refluxed overnight. Usual work-up gave, after column chromatography (silica gel, dichloromethane/methanol, 98:2-95:5), a 5: 1 mixture of two compounds.

1-(2α-Ethyl-1,2,3,4,6,7,12,12bα-octahydroindolo[2,3-a]quinolizin-2-yl)-ethanone:

NMR: 0.82 (t, 3H), 2.14 (s, 3H), 3.44 (br d, 1H), 7.05-7.50 (m, 4H), 8.05 (br s, 1H). MS: 296 (83%), 295 (62%), 253 (100%), 184 (95%).

2-(2α-Ethyl-1,2,3,4,6,7,12,12bα-octahydroindolo[2,3-a]quinolizin-2-yl)-propan-2-ol:

NMR: 1.05 (t, 3H), 1.24 (s, 6H), 3.42 (br d, 1H), 7.05-7.50 (m, 4H), 7.88 (br s, 1H). MS: 312 (48%), 311 (37%), 253 (100%).

EXAMPLE 25

1-(2α-Ethyl-1,2,3,4,6,7,12,12bα-octahydroindolo[2,3-a]quinolizin-2-yl)-ethanol

The ketone obtained in the above reaction was reduced with sodium borohydride in methanol in the usual manner to give the title alcohol as an inseparable mixture of diastereomers.

NMR: 0.95 (t, 3H, minor), 1.18 (t, 3H, major), 3.61 (q, 1H, minor), 3.67 (q, 1H, major). MS: 298 (100%), 297 (64%), 253 (87%).

EXAMPLE 26

2,3,4,5,7,8,13,13b-Octahydro-1H-azepino[1',2'1,2]pyrido[3,4-b]indole (Compound E)

To a solution of 0.20 g (1.2 mmol) of tryptamine in 5.0 ml of xylene was added 0.14 g (1.2 mmol) of ω-caprolactam. The mixture was refluxed for 7 h. After evaporation of the solvent, the residue was dissolved in 5.0 ml of toluene, 0.65 ml of freshly distilled phosphorus oxychloride was added and the reaction mixture was 25 refluxed for 9 h. The solution was evaporated in vacuum and the residue was mixed with a 20% solution of acetic acid (3×10 ml). The solid was filtered off and the aqueous solution was made alkaline (pH 11) with 25% ammonium hydroxide under cooling and extracted with dichloromethane (3×20 ml). To the combined organic layers was added 6.0 ml of 4 M sodium hydroxide and this mixture was refluxed for 1 h. The organic phase was dried over sodium sulfate, the drying agent was filtered off and the filtrate was concentrated to give an oil, which was dissolved in 30 ml of methanol. To the cold solution was added 0.2 g (5.6 mmol) of sodium borohydride. The mixture was stirred at room temperature for 1 h. Water was slowly added and the reaction mixture was extracted with dichloromethane (3×20 ml). The combined organic phases were dried over sodium sulfate, the drying agent was filtered off and the solvent evaporated to give the title compound, which was purified by column chromatography (silica gel, dichloromethane/methanol, 95:5).

NMR: 4.03 (br d, 1H), 7.11-7.46 (m, 4H), 8.05 (br s, 1H). MS: 240 (52%), 239 (100%), 198 (10%), 170 (24%).

EXAMPLE 27

1α-Ethyl-12-methyl-1,2,3,4,6,7,12bβ-octahydroindolo[2,3-a]quinolizin-1-ol

To a solution of 0.05 g (0.1 mmoles) of 1α-ethyl-1β-hydroxy-1,2,3,4,6,7,12,12b,-octahydroindolo[2,3-a]quinolizine and 0.05 g (0.9 mmoles) of KOH in 1.0 ml of acetone was added 0.02 ml (0.3 mmoles) of iodomethane. The reaction mixture was stirred at rt for 1 h. Water was slowly added and the reaction 1 5 mixture was extracted with dichloromethane (3×20 ml). The combined organic phases were dried over sodium sulfate, the drying agent was filtered off and the filtrate was evaporated to give the title compound, which was purified by column chromatography (silica gel, dichloromethane/methanol, 95:5).

NMR: 0.71 (t, 3H), 1.01 (m, 2H), 3.59 (br s, 1H), 3.72 (s, 3H), 7.00-7.50 (m, 4H). MS: 284 (21%), 283 (100%), 185 (60%), 170 (10%).

EXAMPLE 28

1α-Ethyl-12-ethyl-1,2,3,4,6,7,12bβ-octahydro-indolo[2,3-a]quinolizin-1-ol

The procedure of example 27 was repeated, except that iodoethane was used instead of iodomethane.

NMR: 0.71 (t, 3H), 1.00 (m, 2H), 1.07 (t, 3H), 3.60 (s, 1H), 4.20 (m, 1H), 4.64 (m, 1H), 7.00-7.50 (m, 4H). MS: 298 (29%), 297 (19%), 199 (100%), 171 (33%).

EXAMPLE 29

1α-Methyl-1,3,4,5,6,11b-hexahydro-2H-11-oxa4a-aza-benzo[a]fluoren-1-ol

To a solution of 0.48 g (3.0 mmol) of 2-(3-benzo[b]furanyl)ethylamine in 5.0 ml of xylene was added 0.34 g (3.0 mmol)

of α-methyl-δ-valerolactone. The mixture was refluxed for 7.5 h. After evaporation of the solvent the residue was dissolved in 6.0 ml of toluene, 0.72 ml of freshly distilled phosphorus oxychloride was added and the reaction mixture was refluxed for 11 h. The solution was evaporated in vacuum and the obtained oil was mixed with a 20% solution of acetic acid (3×20 ml). The solid was filtered off and the aqueous solution was made alkaline (pH 11) with 25% ammonium hydroxide under cooling and extracted with dichloromethane (3°ml). To the combined organic phases was added 12.5 ml of 4 M sodium hydroxide and this mixture was refluxed for 1 h. The organic phase was dried over sodium sulfate, the drying agent was filtered off and the filtrate was concentrated to give the, corresponding enamine, which was oxidised as described in example 9.

NMR: 1.18 (s, 3H), 3.25 (br d, 1H), 7.10-7.50 (m, 4H). MS: 257 (25%), 242 (10%), 172 (100%).

EXAMPLE 30

(1α-Methyl-1,3,4,5,6,11bβ-hexahydro-2H-11-oxa-4a-aza-benzo[a]fluoren-1-yl)-methanol The procedure of example 29 was repeated, except that to the formed enamine, 40% aqueous formaldehyde was slowly added. The reaction mixture was refluxed for 3.5 h and the solvent was evaporated. The residue was diluted with ethyl acetate and washed with brine. The organic phase was dried over sodium sulfate, the drying agent was filtered off and the filtrate was evaporated to give the title compound, which was purified by column chromatography (silica gel, (dichloromethane/methanol, 98:2).

NMR: 0.89 (s, 3H), 3.40 (br s, 1H), 3.62 (d, 1H), 4.29 (d, 1H), 7.10-7.50 (m, 4H). MS: 271 (69%), 270 (100%), 198 (45%), 171 (52%), 170 (60%).

EXAMPLE 31

1α-Isopropyl-1,3,4,5,6,11b-hexahydro-2H-11-oxa-4a-aza-benzo[a]fluoren-1-ol

The procedure of example 9 was repeated, except that 2-(3-benzo[b]furanyl)ethylamine was used instead of tryptamine.

NMR: 1.00 (m, 611), 7.25 (m, 2H), 7.44 (m, 2H), MS: 285 (23%), 242 (10%), 198 (10%), 186 (23%), 172 (100%).

EXAMPLE 32

1α-Ethyl-1,3,4,5,6,11bβ-hexahydro-2H-11-oxa4a-aza-benzo[a]fluoren-1-ol

The procedure of example 29 was repeated, except that α-ethyl-δ-valerolactone was used instead of α-methyl-δ-valerolactone.

NMR: 0.73 (t, 3H), 3.22 (br s, 1M), 7.00-7.30 (m, 2H), 7.40-7.55 (m, 2H). MS: 271 (15%), 186 (18%), 173 (11%), 172 (100%), 170 (28%).

EXAMPLE 33

(1α-Ethyl-1,3,4,5,6,11bβ-hexahydro-2H-11-oxa-4a-aza-benzo[a]fluoren-1-yl)-methanol The procedure of example 30 was repeated, except that α-ethyl-δvalerolactone was used instead of α-methyl-δ-valerolactone.

NMR: 0.62 (t, 3H), 3.48 (br s, 1H), 3.52 (d, 11), 4.06 (d, 1H), 7.00-7.30 (m, 2H), 7.40-7.55 (m, 2H). MS: 285 (56%), 284 (100%), 268 (19%), 198 (36%), 172 (20%), 171 (44%), 170 (54%).

EXAMPLE 34

5,6,7,7a,11,11b,12-Decahydro-6a,12-diaza-indeno[1,2-a]fluoren-11a-ol

The procedure of example 29 was repeated, except that instead of 2-(3-benzo[b1furanyl)ethylamine and α-methyl-δ-valerolactone, tryptamine and hexahydroisobenzofuran-1-one were used.

NMR: 4.45 (br d, 1H), 7.00-7.60 (m, 4H), 9.11 (br s, 1H). MS: 296 (8%), 143 (100%), 130 (81%).

EXAMPLE 35

1,2,3,4,4a,5,6,7,8,13-Decahydro-6a,13-diaza-indeno[1,2-c]phenanthrene

To a solution of 0.356 g (1.26 mmol) of N-[2-(3-indolyl)ethyl)]decahydroiso-quinoline in 20 ml of ethanol was added a solution of 1.6 g of mercuric acetate and 1.88 g of ethylenediaminetetra-acetic acid disodium salt dihydrate in 40 ml of water and the resulting mixture was refluxed for 3 h. The cooled mixture was made basic with dilute ammoniumhydroxide (pH 11) and then extracted with dichloromethane (3×30 ml). The combined organic layers were dried over sodium sulfate, filtered and the solvent evaporated to give the crude enamine (mixture of regioisomers), which was directly used in the next step (see example 36). The pure enamine could be obtained by column chromatography (silica gel, dichloromethane/methanol/triethylamine, 98:1:1).

EXAMPLE 36

2,3,4,4aβ,5,6,7,8,13,13bβ-Decahydro-1H-6a,13-diaza-indeno[1,2-c]phenanthren-13cβ-ol (Compound F)

As in example 9, 0.42 g (1.51 mmol) of the crude enamine from example 35 was treated with 0.21 g of potassium iodide and 0.32 g of iodine in 30 ml of acetonitrile. After reduction with 0.29 g of sodium borohydride in 30 ml of methanol, the crude product was purified by column chromatography (silica, dichloromethane/methanol, 99:1) to afford the pure alcohol.

NMR: 3.18 (br s, 1H), 7.0-7.55 (m, 4H), 9.18 (br s, 1H). MS: 296 (25%), 295 (10%), 185 (15%), 171 (100%).

EXAMPLE 37

(2,3,4,4aβ,5,6,7,8,13,13bβ-Decahydro-1H-6a,13-diaza-indeno[1,2-c]phenanthrenyl)-13cβ-methanol A solution of 150 mg (1.51 mmol) of the above pure enamine (from example 35), 2 ml of 36% aqueous formaldehyde and 0.2 ml N-ethyldiisopropylamine in 10 ml of acetonitrile was refluxed for 3 h. After work-up the crude product was purified by column chromatography (silica gel, dichloromethane/methanol, 98:2) to afford the pure alcohol.

NMR: 3.29 (br s, 1H), 3.98 (d, 1H), 4.17 (d, 1H), 7.0-7.5 (m, 4H), 10.05 (br s, 1H). MS: 310 (88%), 309 (100%), 293 (34%), 197 (67%), 184 (35%), 170 (90%), 169 (77%).

EXAMPLE 38

3β,4α-Dimethyl-1,2,3,4,6,7,12,12bβ-octahydro-indolo[2,3-a]quinolizine

To a solution of 0.422 g (1.65 mmol) of N-[2'-(3'-indolyl)ethyl)]-2,3-dimethylpiperidine in 25 mnl of ethanol was added 2.1 g of mercuric acetate and 2.46 g of ethylenediaminetetraacetic acid disodium salt dihydrate in 50 ml of water and the resulting mixture was refluxed for 3 h. The cooled mixture was made basic with dilute ammoniumhydroxide and then extracted with dichloromethane. Drying over sodium sulfate, filtration and evaporation of the solvent gave the crude enamine, which was dissolved in 30 ml methanol and cooled with an ice bath. A few drops of acetic acid were added followed by 0.322 g of sodium borohydride in portions. After stirring for 1.5 h, the mixture was worked up in the usual manner to give the crude product, which was purified by column chromatography (silica gel, dichloromethane/methanol (98.5:1.5).

NMR: 0.89 (d, 3H), 0.96 (d, 3H), 3.76 (br d, 1H), 7.0-7.5 (m, 4H), 7.71 (br s, 1H). MS: 254 (95%), 253 (100%), 239 (30%), 170 (31%), 169 (36%).

EXAMPLE 39

(1α-Ethyl-1,2,3,4,6,7,12,12bβ-octahydroindolo[2,3-a]-quinolizin-1-ylmethoxy)-acetic acid ethyl ester A solution of 0.02 g (0.07 mmol) of (1β-ethyl-1,2,3,4,6,7,12,12bα-octahydro-indolo[2,3-a]quinolizin-1-yl)-methanol (*Gazz. Chim. Ital.* 111 (1981) 257-267) in N,N-dimethylformamide-toluene (1 ml, 1:1) was added to 6.8 mg (0.28 mmol) of sodium hydride, previously washed with heptane. The reaction mixture was stirred at rt for 1 h and then ethyl bromoacetate (0.009 mnl, 0.084 mmol) in toluene (1 ml) was added dropwise. The stirring was continued for 3 h at rt. Water was slowly added and the reaction mixture was extracted with dichloromethane (3×20 ml). The combined organic phases were dried over sodium sulfate, the drying agent was filtered off and the filtrate was evaporated to give the title compound, which was purified by column chromatography (silica gel, dichloromethane/methanol, 5:5).

NMR: 0.61 (t, 3H), 1.28 (t,3H), 3.49 (s, 1H), 4.25 (d, 1H), 4.30 (q, 2H), 4.55 (d, 1H), 6.93 (t, 1H), 7.03 (t, 1H), 7.35 (d, 1H), 7.38 (d, 1H), 10.64(s, 1H). MS: 370 (40%), 369 (30%), 283 (12%), 267 (100%), 197 (12%), 170 (12%), 169 (16%)

EXAMPLE 40

5,6,7,7aβ,8,9,10,11,11aβ,11bαc-Decahydro-12-oxa-6a-aza-indeno[1,2-a]fluorene

To a solution of 0.70 g (0.43 mmol) of 2-(3-benzo[b]furanyl)ethylamine in 30 ml of chlorobenzene was added 0.13 g (0.87 mmol) of cis-1,2-cyclohexanedicarboxylic anhydride. The mixture was irradiated in a microwave oven (1000 W, T=130° C.) for 30 min. Chlorobenzene was replaced by ethanol (5 ml) and 82.7 mg (2.18 mmol) of sodium borohydride was added. The mixture was stirred at rt for 18 h, after which water was added and the product was isolated in the usual manner. Trifluoroacetic acid (0.12 ml, 1.53 mmol) in dichloromethane (10 ml) was added and the reaction mixture was stirred for 2 h at rt. Alkaline work-up (4 M sodium hydroxide), gave the amide intermediate, which was dissolved in diethyl ether (15 ml), 0.1 g (2.63 mmol) of lithium aluminum hydride was added and the reaction mixture was refluxed for 1.5 h. Water was slowly added under cooling. After normal extraction procedures, the crude product was purified by column chromatography (silica gel, dichloromethane/methanol, 90:10).

NMR: 1.77 (m, 2H), 2.07 (m, 1H), 2.29 (m, 1H), 2.48 (m, 1H), 3.04 (m, 1H), 3.20 (m, 1H), 4.13 (s, 1H), 7.18-7.50 (m, 4H). MS: 267 (46%), 266 (100%), 185 (52%), 170 (12%).

EXAMPLE 41

1-Methyl-1α,3,4,6,11bβ-hexahydro-2H-11-oxa4a-aza-benzo[a]fluorene (Compound G)

The procedure of example 26 was repeated, except that α-methyl-δ-valerolactone and 2-(3-benzo[b]furanyl)ethylamine were used instead of ε-caprolactam and tryptamine, respectively.

NMR: 0.88 (d, 3H), 3.34 (br s, 1H), 7.19-7.43 (m, 4H). MS: 241 (40%), 240 (50%), 226 (100%), 198 (10%), 170 (68%), 170 (24%).

EXAMPLE 42

(1-Hydroxymethyl-1,3,4,5,6,11b-hexahydro-2H-11-oxa4a-aza-benzo[a]fluoren-1-yl]-methanol The procedure of example 41 was repeated, except that δ-valerolactone was used instead of a-methyl-δ-valerolactone, and the obtained enamine was treated With formaldehyde as in example 14.

NMR: 3.30 (d, 1H), 3.76 (d, 1H), 3.79 (d, 1H), 3.82 (s, 1H), 4.31 (d, 1H), 7.18-7.50 (m, 4H). MS: 287 (56%), 286(60%), 270(40%), 256 (100%), 198 (34%), 172 (26%), 170 (54%).

EXAMPLE 43

1-Methoxymethyl-1α-methyl-1,3,4,5,6,11bβ-hexahydro-2H-11-oxa-4a-aza-benzo[a]fluorene A solution of 173.1 mg (0.64 mmol) of the alcohol described in example 30 in 5 ml of tetrahydrofuran was added to 153.0 mg (6.38 mmol) of sodium hydride, previously washed with heptane. The reaction mixture was stirred at 35° C. for 1 h followed by dropwise addition of a solution of 0.04 ml (0.64 mnmol) of iodomethane in tetrahydrofuran (5 ml). The stirring was continued for 1 h. Water was slowly added and the reaction mixture was extracted with dichloromethane (3×20 ml). The combined organic phases were dried over sodium sulfate, the drying agent was filtered off and the filtrate was evaporated to give the title compound, which was purified by column chromatography (silica gel, dichloromethane/methanol, 90: 10).

NMR: 0.74 (s, 3H), 3.29 (s, 3H), 3.36 (d, 1H), 3.89 (d, 1H), 7.20-7.52 (m, 4H). MS: 285 (80%), 284 (100%), 270 (20%), 254 (98%), 198 (35%), 171 (82%), 170 (70%).

EXAMPLE 44

2,3,4,4aβ,5,6,7,8,13bβ,13co-Decahydro-1H-13-oxa-6a-aza-indeno[1,2-c]phenanthrene and 2,3,4,4a,5,6,7,8,13bα,13cβ-decahydro-1H-13-oxa-6a-aza-indeno[1,2-c]phenanthrene The procedure of example 41 was repeated, except that cis-octahydro-isochromen-1-one was used instead of 1-methyl-δ-valerolactone. The two isomers were separated by column chromatography (silica gel, ethyl acetate/heptane, 70:30). 2,3,4,4aβ,5,6,7,8,13bβ,13cβ-Decahydro-1H-13-oxa-6a-aza-indeno[1,2-c]phenanthrene:

NMR: 3.28 (s, 1H), 7.17-7.53 (m, 4H). MS: 281 (40%), 280 (100%), 238 (15%), 198 (12%), 170 (24%).

2,3,4,4aβ,5,6,7,8,13bα,13cβ-decahydro-1H-13-oxa-6a-aza-indeno[1,2-c]phenanthrene:

NMR: 2.75 (d, 1H), 7.15-7.43 (m, 4H). MS: 281 (38%), 280 (100%), 198 (16%), 170 (30%).

EXAMPLE 45

1α-Methyl-1,3,4,5,6,11bα-hexahydro-2H-11-oxa-4a-aza-benzo[a]fluorene-1-carboxylic acid ethyl ester To a mixture of 0.375 g (2.33 mmol) of 2-(3-benzo[b]furanyl)ethylamine and triethylamine (0.97 ml, 7.0 mmol) in dichloromethane (3 ml) was added 0.56 g (2.33 mmol) 5-chloro-2-ethoxycarbonyl-2-methylvaleroyl chloride (prepared according to the process described for the corresponding 2-ethyl derivative in *J. Org Chem.* 45 (1980) 32-34) in dichloromethane (4 ml). After stirring at rt for 45 min, water was added and the mixture was extracted with dichloromethane. Drying over sodium sulfate, filtration of the drying agent and evaporation of the solvent gave the crude amide, which was purified by column chromatography (ethyl acetate/heptane, 1:1). The pure amide (0.3 g, 0.82 mmol) was dissolved in toluene (3 ml) and 0.38 ml (4.1 mmol) of phosphorus oxychloride was added. The mixture was refluxed for 2 h, after which it was evaporated to dryness. The residue was dissolved methanol (3 ml) and 57 mg (1.5 mmol) of sodium borohydride was added in portions. After stirring at rt for 1 h, water was added and the mixture was extracted with ethyl acetate. Drying over sodium sulfate, followed by filtration and evaporation gave the crude ester which was purified by column chromatography (silica gel, ethyl acetate/heptane, 1:1).

NMR: 0.65 (t, 3H), 1.55 (s, 3H), 3.30 (br s, 1H), 7.16-7.50 (m, 4H). MS: 313 (70%), 312 (100%), 284 (22%), 240 (32%), 198 (80%), 171 (35%), 170 (95%).

EXAMPLE 46

1-Ethoxymethyl-1α-methyl-1,3,4,5,6,11bβ-hexahydro-2H-11-oxa-4a-aza-benzo[a]fluorene The procedure of example 43 was repeated, except that iodoethane was used instead of iodomethane.

NMR: 0.74 (s, 3H), 1.17 (t, 3H), 3.37 (s, 1H), 3.38 (d, 1H), 3.54 (q, 2H), 3.96 (d, 1H), 7.10-7.60 (m, 4H). MS: 299 (70%), 298 (92%), 270 (40%), 254 (100%), 198 (34%), 171 (86%), 170 (72%).

EXAMPLE 47

(1β-Methyl-1,3,4,5,6,11bα-hexahydro-2H-11-oxa-4a-aza-benzo[a]fluoren-1-yl)-methanol To a suspension of 0.31 g (8.23 mmol) of lithium aluminum hydride in dry tetrahydrofuran (10 ml), was added 0.86 g (2.74 mmol) of the ester described in example 45 in dry tetrahydrofuran (10 ml). The reaction mixture was refluxed for 1 h. Water was slowly added and the reaction mixture was extracted with ethyl acetate (3×20 ml). The combined organic phases were dried over sodium sulfate, filtered and the filtrate was evaporated to give the desired product, which was purified by column chromatography (silica gel, ethyl acetate/heptane, 50:50).

NMR: 1.30 (s, 3H), 2.98 (br s, 1H), 3.21 (d, 1H), 3.69 (d, 1H), 4.33 (s, 1H), 7.15-7.55 (m, 4H). MS: 271 (52%), 270 (100%), 198 (34%), 172 (20%), 171 (44%), 170 (66%).

EXAMPLE 48

(1α-Methyl-1,2,3,4,6,7,12,12bα-octahydroindeno[2,1-a]quinolizin-1-yl)-methanol

The procedures described in examples 45 and 47 were repeated, except that 2-(3H-inden-1-yl)-ethylamine was used instead of 2-(3-benzo[b]furanyl)ethylamine.

NMR: 0.82 (s, 3H), 3.07 (br s, 1H), 3.23 (d, 1H), 3.39 (d, 1H), 3.52 (d, 1H), 3.70 (d, 1H), 7.05-7.35 (m, 4H). MS: 269 (43%), 268 (100%), 252 (29%), 196 (36%), 168 (40%).

EXAMPLE 49

1α-Ethyl-1,3,4,5,6,11bα-hexahydro-2H-11-oxa-4a-aza-benzo[a]fluorene-1-carboxylic methyl ester The procedure of example 45 was repeated, except that 5-chloro-2-ethoxycarbonyl-2-ethylvaleroyl chloride was used instead of 5-chloro-2-ethoxycarbonyl-2-methylvaleroyl chloride.

NMR: 0.90 (t, 3H), 6.90-7.58 (m, 4H). MS: 327 (72%), 326 (100%), 312 (20%), 298 (20%), 254 (30%), 198 (54%), 172 (60%), 170 (90%).

EXAMPLE 50

1-Methoxymethyl-1α-methyl-1,3,4,,5,6,11bα-hexahydro-2H-11-oxa-4a-aza-benzo[a]fluorene The procedure of example 43 was repeated, except that the alcohol described in example 47 was used as the starting compound.

NMR: 1.44 (s, 3H), 2.99 (d, 1H), 3.15 (br s, 1H), 3.22 (s, 3H), 3.70 (d, 1H), 7.18-7.50 (m, 4H). MS: 285 (84%), 284 (100%), 270 (14%), 254 (92%), 198 (34%), 171 (74%), 170 (50%).

EXAMPLE 51

(1α-Ethyl-1,3,4,5,6,11bα-hexahydro-2H-11-oxa-4a-aza-benzo[a]fluorene-1-yl)-methanol The procedure of example 47 was repeated, except that the ester described in example 49 was used as the starting compound.

NMR: 1.00 (t, 3H), 2.93 (m, 2H), 3.29 (s, 1H), 7.15-7.60 (m, 4H). MS: 286 (90%), 285 (68%), 284 (100%), 268 (16%), 198 (22%), 171 (22%), 170 (36%).

EXAMPLE 52

1-β-Hydroxymethyl-1-methyl-1,2,3,4,6,7,12,12bα-octahydro-indolo[2,3-a]quinolizine-6β-carboxylic acid methyl ester The procedure of the preparation of (1β-ethyl-1,2,3,4,6,7,12,12bα-octahydro-indolo[2,3-a]quinolizin-1-yl)-methanol (*Gazz. Chim.* 111 (1981) 257-267) was repeated, except that L-tryptophan methyl ester was used instead of tryptamine.

NMR: 0.74 (s, 3H), 3.39 (s, 3H), 3.46 (d, 1H), 3.97 (d, 1H), 4.38 (br s, 1H), 7.00-7.50 (m, 4H), 8.90 (br s, 1H). MS: 328 (26%), 327 (100%), 299 (38%), 268 (32%), 170 (10%), 169 (24%).

EXAMPLE 53

Resolution of 1α-isopropyl-1,2,3,4,6,7,12,12bβ-octahydroindolo[2,3-a]quinolizin-1-ol A solution of 0.3 g (1.1 mmol) of (±)-1α-isopropyl-1,2,3,4,6,7,12,12bβ-octahydroindolo[2,3-a]quinolizin-1-ol and 0.16 g (1.1 mmol) of L-tartaric acid in 15 ml of acetone was refluxed for 30 min. On standing at room temperature overnight there was deposited of 200 mg of a solid. After two recrystallizations from methanol the collected L-tartrate salt was partitioned between dichloromethane and 10% sodium hydroxide solution, dried over sodium sulfate and evaporated to yield 116.6 mg of (−)-1α-isopropyl-1,2,3,4,6,7,12,12bβ-octahydroindolo[2,3-a]quinolizin-1-ol with $[\alpha]_D = -64.50°$ (c, 0.011 in $CHCl_3$). The other enantiomer (+)-1α-isopropyl-1,2,3,4,6,7,12,12bβ-octahydroindolo[2,3-a]quinolizin-1-ol $[a]_D = +64.5°$ (c, 0.011 in $CHCl_3$) was isolated from the mother liquor in the same manner.

EXAMPLE 54

Resolution of (1α-methyl-1,3,4,5,6,11bβ-hexahydro-2H-11-oxa-4a-aza-benzo[a]fluoren-1-yl)-methanol The procedure of example 53 was repeated, except that (+)-diacetyl-L-tartaric anhydride and isopropanol were used instead of L-tartaric acid and acetone. Optical purities of the separated enantiomers were confimed by chiral HPLC (column: DAICEL CHEMICAL INDUSTRIES, LTD CHIRACEL OJ, dimension 0.46 cm * 25 cm, flow: 0.5 mlmin, mobile phase: n-hexane (Merck Uvasol for Spectroscopy)/isopropanol (Rathburn, HPLC-grade) (100:20), UV detection at 272 nm, retention times: 8.8 min [(+)-(1α-methyl-1,3,4,5,6,11bβ-hexahydro-2H-11-oxa-4a-aza-benzo[a]fluoren-1-yl)-methanol]and 11.1 min [(−)-(1α-methyl-1,3,4,5,6,11bβ-hexahydro-2H-11-oxa4a-aza-benzo[a]fluoren-1-yl)-methanol].

EXAMPLE 55

Resolution of (1α-methyl-1,3,4,5,6,11bα-hexahydro-2H-11-oxa-4a-aza-benzola]fluoren-1-yl)-methanol The procedure of example 53 was repeated, except that (−)-di-p-toluoyl-L-tartaric acid monohydrate and ethyl acetate were used instead of Lrtartaric acid and acetone. Optical purities of the separated enantiomers were confirmed by chiral HPLC (column: DAICEL CHEMICAL INDUSTRIES, LTD CHIRACEL OJ, dimension 0.46cm25 cm, flow: 0.8 ml/min, mobile phase: n-hexane (Merck Uvasol for Spectroscopy)/isopropanol (Rathburn, HPLC-grade) (180:20), UV detection at 254 nm, retention times: 7.8 min [(+)-(1-methyl-1,3,4,5,6,11bα-hexahydro-2H-1-oxa-4a-aza-benzo[a]fluoren-1-yl)-methanol] and 12.6 min [(−)-(1α-methyl-1,3,4,5,6,11boc-hexahydro-2H-11-oxa-4a-aza-benzo[a]fluoren-1-yl)-methanol].

EXAMPLE 56

Enantiomers of 1-methoxymethyl-10-methyl-1,3,4,5,6,11bβ-hexahydro-2H-11-oxa-4a-aza-benzo[a]fluorene The procedure of example 43 was repeated, except that pure enantiomers, (+)-(1α-methyl-1,3,4,5,6,11bβ-hexahydro-2H-11-oxa-4a-aza-benzo[a]fluoren-1-yl)-methanol and (−)-(1α-1α-methyl-1,3,4,5,6,11bβ2-hexahydro-2H-11-oxa-4a-aza-benzo[a]fluoren-1-yl)-methanol, respectively, from example 54 were used instead of the alcohol described in example 30. Optical purities of the products were confirmed by chiral HPLC (column: ROCKLAND TECHNOLOGIES, INS ULTRON ES-OVM, dimension 4.6 cm*15 cm, flow: 0.8 ml/min, mobile phase: 0.04 M $KH_2PO_4$ (pH 4.6)/acetonitrile (Merck Lichrosolv Isocratic grade for liquid. chromatography) (90:10), retention times 3.8 min [(−)-1-methoxymethyl-1x-methyl-1,3,4,5,6,11bβ-hexahydro-2H-11-oxa4a-aza-benzo[a]fluorene] and 5.8 min [(+)-1-methoxymethyl-1α-methyl-1,3,4,5,6,11bβ-hexahydro-2H-11-oxa-4a-aza-benzo[a]fluorene].

EXAMPLE 57

Enantiomers of 1-methoxymethyl-1α-methyl-1,3,4,5,6,11bα-hexahydro-2H-11-oxa-4a-aza-benzo[a]fluorene The procedure of example 43 was repeated, except that pure enantiomers, (+)-(1α-methyl-1,3,4,5,6,11bα-hexahydro-2H-11-oxa-4a-aza-benzo[a]fluoren-1-yl)-methanol and (−)-(1α-methyl-1,3,4,5,6,11bα-hexahydro-2H-11-oxa-4a-aza-benzo[a]fluoren-1-yl)-methanol, respectively, from example 55 were used instead of the alcohol described in example 30. Optical purities of the products were confirmed by chiral HPLC (column: DAICEL CHEMICAL INDUSTRIES, LTD CHIRACEL OJ, dimension 0.46 cm*25 cm, flow: 0.8 ml/min, mobile phase: n-hexane (Merck Uvasol for Spectroscopy), retention times 5.6 min [(+)-1-methoxymethyl-1α-methyl-1,3,4,5,6,11bα-hexahydro-2H-11-oxa-4a-aza-benzo[a]fluorene] and 6.3 min [(−)-1-methoxymethyl-1-1α-methyl-1,3,4,5,6,11bα-hexahydro-2H-11-oxa-4a-aza-benzo[a]fluorene].

The following known compounds can be prepared analogously or according to the methods known in the literature.

1α-Methyl-1,2,3,4,6,7,12,12bβ-octahydroindolo[2,3-a]quinolizin-1-ol (Compound H): The procedure of example 6 was repeated, except that 1-ethyl-4,9-dihydro-3H-pyrido[3,4-b]indole (*J. Chem. Soc., Perkin Trans I* (1977) 2109-2115) was used instead of -isobutyl-4,9-dihydro-3H-pyrido[3,4-b] indole.

2β-Methyl-1,2,3,4,6,7,12,12bβ-octahydroindolo[2,3-a] quinolizin-2-ol and 2α-methyl-1,2,3,4,6,7,12,12bβ-octahydro-indolo[2,3-a]quinolizin-2-ol are prepared following the procedures described in *J. Org. Chem.* 56 (1991) 2701-2712 and *Chem. Ber.* 106 (1973) 3106-3118. 1,2,3,4,5,7,12,12bβ-Octahydroindolo[2,3-a]quinolizin-1α-ol and 1,2,3,4,6,7,12,12bβ-octahydrindolo[2,3-a]quinilizin-1β-ol are prepared according to the method described in *J. Chem. Soc., Chem. Comm.*, (1972) 461. 1,4,6,7,12,12b-Hexahdroindolo[2,3-a]quinolizine (Compound I) is prepared according to the method described in *Tetrahedron* 45 (1989) 3975-3992. 3,4,6,7,12,12b-Hexahydroindolo[2,3-a]quinolizine and 1-ethyl-3,4,6,7,12,12b-hexahydroindolo[2,3-a]quinolizine are prepared according to the method described in *Bull. Soc. Chim. Fr.* 7-8 (1976) 1222. 1α-Ethyl-1,2,3,4,6,7,12,12bβ-octabydroindolo[2,3-a]quinolizine and 1β-ethyl-1,2,3,4,6,7,12,12bβ-octabydroindolo[2,3-a]quinolizine (Compound J) are prepared according to the method described in *Tetrahedron* 45 (1989) 7615-7630. 1α-Ethyl-1,2,3,4,6,7,12,12bβ-octahydroindolo[2,3-]quinolizin-1-ol (Compound K) and (10-ethyl-1,2,3,4,6,7,12,12box-octahydroindolo[2,3-alquinolizin-1-yl)-methanol (Compound L) are prepared according to the method described in *Gazz. Chim. Ital.* 111 (1981)

257-267. (1β-Ethyl-1,2,3,4,6,7,12,12bβ-octahydroindolo[2,3-a]quinolizin-1-yl)-methanol (Compound M) is prepared according to the method described in *Indian J Chem., Sect. B* 22 (1983) 531. 3-Ethyl-2-methyl-1,4,6,7,12,12b-hexahydroindolo[2,3-a]quinolizine (Compound N) and 3α-ethyl-2α-methyl-1,2,3,4,6,7,12,12b-octahydroindolo[2,3-a]quinolizine are prepared according to the method described in *Tetrahedron* 46 (1990) 2633-2650. 2,3,5,6,7,11,11b-Hexahydro-1H-indolizino 8,7-b]indolo is prepared according to the method described in *J. Org. Chem.* 53 (1988) 4236. (1β,2,3,4,6,7,12,12bα-Octahydroindolo'[2,3-a]quinolizin-1-yl)-methanol (Compound O) is prepared by reduction of the corresponding ester which synthesis is described in *Tetrahedron* 52 (1996) 9925. 1-(1α2,3,4,6,7,12 12bβ-Octahydroindolo[2,3-a]quinolizin-1-yl)-ethanol (Compound P) is prepared by reduction of its corresponding ketone which synthesis is described in *Tetrahedron Lett.* 30 (1989) 719. 1β-Propyl-1,2,3,4,6,7,12,12bβ-octahydro-indolo[2,3-a]quinolizine is prepared according to the method described in *J Org. Chem.* 34 (1969) 330. 1α-Ethyl-1β-methyl-1,2,3,4,6,7,12,12bβ-octahydroindolo[2,3-a]quinolizine is prepared according to the method described in *J Chem. Res.* (S) (1995) 382. 2β-Tert-butyl-1,2,3,4,6,7,12,12bβ-octahydroindolo[2,3-a]quinolizine and 2β-tert-butyl-1,2,3,4,6,7,12,12bα-octahydro-indolo[2,3-a]quinolizine (Compound Q) are prepared according to -the method described in Tetrahedron 45 (1989) 3975. 2-tert-Butyl-1,4,6,7,12,12b-hexahydroindolo[2,3-a]quinolizine and 2-tert-butyl-3,4,6,7,12,12b-hexahydro-indolo[2,3-a]quinolizine are prepared according to the method described in Tetrahedron 47 (1991) 2879-2894. (−)-1α-Ethyl-1,2,3,4,6,7,12,12bβ-octahydroindolo[2,3-a]quinolizin-1ol and (+)-1α-ethyl-1,2,3,4,6,7,12,12bβ-octahydroindolo[2,3-a]quinolizin-1-ol are obtained by resolution of their racemic mixture (Compound K).

As already mentioned hereinbefore, the compounds of the present invention show interesting pharmacological properties, namely they exhibit affinity for alpha2 adrenoceptors. The said pharmacological activity of the compounds of the invention is demostrated with the pharmacological tests presented below.

EXPERIMENT I

Radioligand Binding to Alpha2-Adrenoceptors

Examples of the alpha2-adrenoceptor binding affinities of the compounds including in the present invention are shown in the Table 1. Many of these compouinds are high-affinity ligands for all the alpha2-receptors, but some of them display selectivity for the alpha2C-subtype.

TABLE 1

Calculated Ki values from radioligand binding assays

| Compound | Binding affinity (Ki; nM) | | |
|---|---|---|---|
| | alpha2A | alpha2B | alpha2C |
| A | 480 | 330 | 61 |
| B | 130 | 160 | 25 |
| C | 710 | 580 | 87 |
| D | 29 | 81 | 17 |
| E | 30 | 110 | 26 |
| F | 514 | not measured | 70 |
| G | 96 | not measured | 22 |
| H | 280 | 45 | 23 |
| I | 150 | 460 | 85 |
| J | 210 | 520 | 75 |

TABLE 1-continued

Calculated Ki values from radioligand binding assays

| Compound | Binding affinity (Ki; nM) | | |
|---|---|---|---|
| | alpha2A | alpha2B | alpha2C |
| K | 359 | 245 | 31 |
| L | 85 | 20 | 18 |
| M | 440 | 470 | 110 |
| N | 130 | 1110 | 46 |
| O | 380 | 270 | 110 |
| P | 290 | 410 | 90 |
| Q | 27 | 40 | 6.4 |

EXPERIMENT II

In vitro Antagonism on the Alpha2-adrenoceptors

The functional activities of two compounds (K and L) displaying alpha2C-selectivity in binding experiments were determined as the abilities of the compounds to inhibit the epinephrine-stimulated binding of $^{35}$S-GTPγS to G proteins (Jasper, J. R. et al., *Biochem. Pharmacol.* 55(7) (1998) 103544) in membranes of CHO cells stably transfected with the human alpha2-adrenoceptor subtypes. The antagonist potencies of compound K and compound L are presented in the Table 2. The results show that these compounds are selective antagonists for the alpha2C-subtypes.

TABLE 2

The mean antagonist potencies ($K_B$) of compound K and compound L on the human alpha2-adrenoceptor subtypes.

| Compound | Antagonist potency ($K_B$; nM) | | |
|---|---|---|---|
| | alpha2A | alpha2B | alpha2C |
| K | 295 | 351 | 23 |
| L | 320 | 75 | 4.2 |

In vivo Effects of Alpha2C-selective Compounds

It is currently not well-known in the art what effects in vivo could be attributed to a selective alpha2C-antagonism. Based on available knowledge and our previous experience, we have selected two different behavioral models, namely d-amphetamine—stimulated locomotor activity model and the forced swimming test, in order to demonstrate specific alpha2C-antagonistic effects in the CNS of mice and rats in vivo. The selection of these methods is essentially based on published hypotheses on theoretical effects of alpha2C-antagonists; in the lack of suitable ligands, these hypotheses were based on studies employing mice with genetically 20 altered alpha2C-adrenoceptor expression (Scheinin, M. et al., *Life Sci* 68(19-20) (2001) 2277-85).

EXPERIMENT III

D-amphetamine Stimulated Locomotor Ativity Test

Genetically modified mice having non-finctional alpha2C-adrenoceptors (alpha2C-"knockout"; alpha 2C-KO) are more sensitive to the locomotor-enhancing effects of the psychostimulant d-amphetamine and, on the other-hand, over-expression of the alpha2C-adrenoceptor in mice (alpha2C-OE)

leads to an opposite effect, i.e. to attenuation of the stimulant effect (Scheinin, M. et al., *Life Sci* 68(19-20) (2001) 2277-85). Thus, it could be hypothesized that alpha2C-antagonist would potentiate the locomotor effects of d-amphetamine.

Figure 1A:
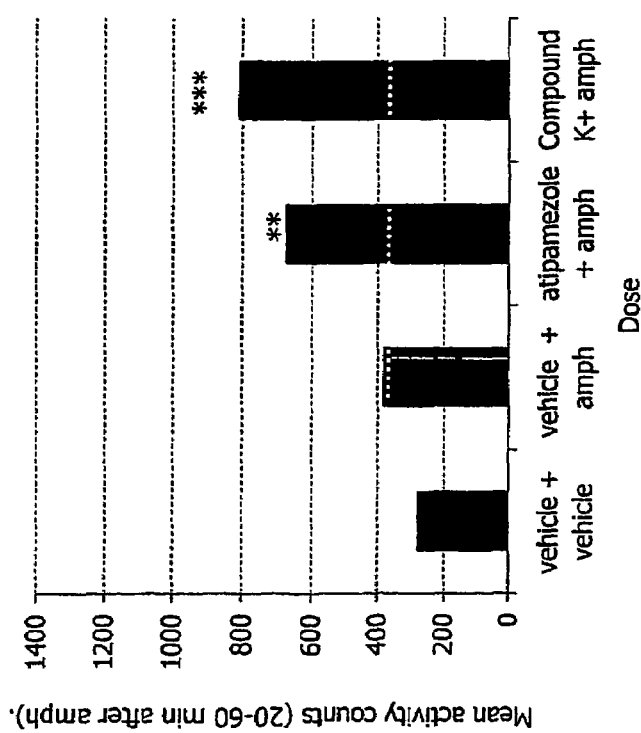

The above assugiipition was tested by administer groups of mice (n=10–12/dose group) anpheampine (4 micromol/kg sc.) either alone or together with the alpha2C$_1$-antagonists (3 micromol/kg s.c.) of this invention or with the alpha2-subtype non-selective potent alpha2-antagonist (1 micromol/kg s.c.) (Haapalinna, A. et al., *Naunyn-Schmiedeberg's Arch. Pharmacol.* 356 (1997) 570-582), and by subsequently measuring the locomotor activity of mice with an automated infrared photobeam system designed for activity studies (PAS CageRack, SanDiego Instruments, San Diego, Calif., USA). As expected, both of the tested alpha2C-selective antagonists increased the activity of mice (FIG. 1*a+b*), as was expected for alpha2C-antagonist. The subtype non-selective alpha2-antagonist also potentiated the d-amphetamine effect. The tested compounds did not affect the baseline locomotor activity of mice (at doses between 0.1-10 mg/kg s.c.).

EXPERIMENT IV

Antagonism of Alpha2-agonist—induced Sedation

Figure 2:
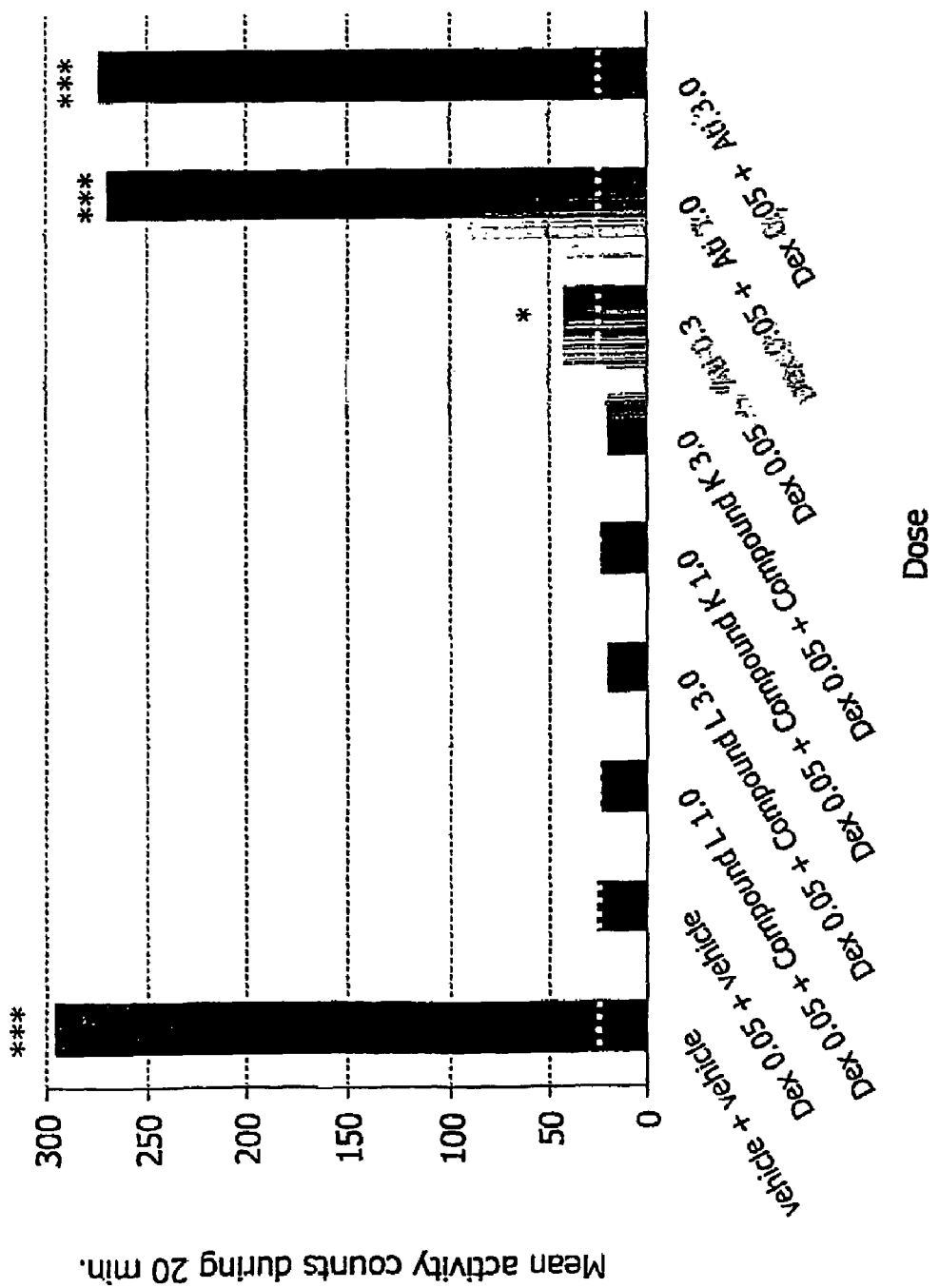
FIG. 2 shows alpha2-agonist-induced sedation (measured as locomotor inhibition) in mice. The non-selective alpha-antagonist atipamnezole (Ati) antagonised the sedative effects of the alpha2-subtype non-selective agonist, dexmedetomidine (Dex; 50 nmol/kg s.c.), while the alpha2C-selective antagonists did not have significant effects. (veh=vehicle). (*** $p<0.001$, compared to Dex+vehicle)

One of the prominent effects of non-selective alpha2-agonists in rodents is their ability to cause profound sedation. This effect, measured as locomotor inhibition by the alpha2-agonist dexmedetomidine was not modified in mice with genetically altered alpha2C-expression (Scheinin, M. et al., *Life Sci* 68(19-20) (2001) 2277-85). On the other hand, alpha2-agonist did not have sedative effect in mice with genetically disrupted alpha2A-adrenoceptor (Hunter, J. C. et al., *British Journal Pharmacology* 122(7) (1997) 1339-44). Therefore, since the sedative effect of alpha2-agonists as generally attributed to the alpha2A-adrenoceptor, it is expected that alpha2C-antagonists would not modulate significantly the alpha2-agonist-induced sedation. This assumption was tested in experiment, where dexmedetomidine was administered to mice pre-treated with the alpha2C-antagonists compound K or compound L, or the subtype non-selective antagonist atipamezole (Haapalinna, A. et al., *Naunyn-Schmiedeberg's Arch. Pharmacol.* 356 (1997) 570-582). As expected, the alpha2C-antagonists did not have clear effects, whereas atipamezole effectively antagonised the effect of dexmedetomidine. This result demonstrates the lack of alpha2A-antagonism of the alpha2C-selective compounds of the present invention (FIG. 2).

EXPERIMENT V

Forced Swimming Test

Figure 3:
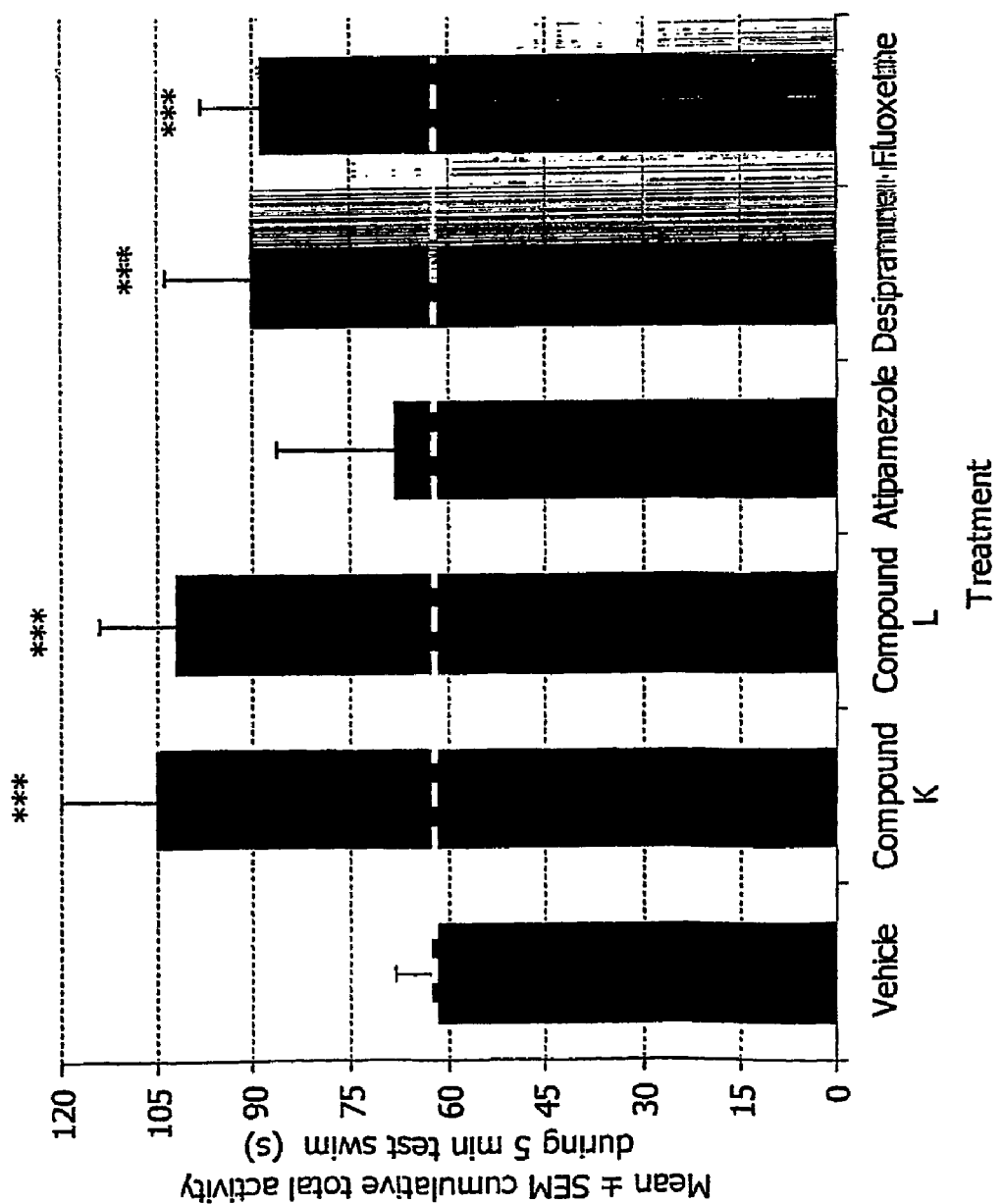
FIG. 3 shows the effect of the alpha2C-selective antagonists compound K (3 micromol/kg) and compound L (3 micromol/kg), the non-selective antagonist atipamezole (10 micromol/kg) and the reference antidepressants desipramine (10 micromol/kg) and fluoxetine (10 micromol/kg) in the forced swimming test in rats. All compounds, except atipamezole, increased activity (*** $p<0.001$, compared to vehicle).

Forced swimming test (FST, i.e. Porsolt's test) is generally used in the pharmacological screening of new-antidepressants. In this test, antidepressants increase the animals' activity compared to non-treated controls. Alpha2C-KO mice appeared to be more active, and alpha2C-OE mice were less active in FST (U.S. Pat. No. 5,902,807 and Scheinin, M. et al., *Life Sci* 68(19-20) (2001) 2277-85). Therefore, it was tested, whether a selective alfa2C-antagonist would have antidepressant-like activity (e.g. activity-increasing property) in the FST. The FIG. 3 shows how both of the alpha2C-compounds increased activity in this test as was expected based on studies on transgenic mice (Scheinin, M. et al., *Life Sci* 68(19-20) (2001) 2277-85) and as reported with recently developed alpha2C-antagonist (WO 01/64645). Also the positive control substances desipramine and fluoxetine (clinically effective antidepressant agents) were active. The subtype non-selective alpha2-antagonist atipamezole did not possess antidepressant-like effect, as expected (WO 01/64645).

EXPERIMENT VI

Prepulse Inhibition of the Startle Reflex

Prepulse-inhibition (PPI) of a startle response refers to the reduction in the startle response caused by a low intensity non-startling stimulus (the prepulse) which is presented shortly before the startle stimulus. PPI can be used as an operational measure of sensorimotor gating and appears to be present in all mammals, including rats and humans (Swerdlow, N. R. et al., *The archives of general psychiatry* 51 (1994) 139-154). Normally finctioning PPI can be disrupted by psychostimulants, such as d-amphetamine or phencyclidine (PCP), and reversed by clinically effective antipsychotics.

In a previous study, alpha2C-KO mutation was associated with weakened PPI whereas alpha2C-OE demonstrated increased PPI. In other words, the genetically altered alpha2C-expression in mice was associated with changes in PPI in a way suggesting that an alpha2C-antagonist would decrease PPI (Scheinin, M. et al., *Life Sci* 68(19-20) (2001) 2277-85). This hypothesis was tested with compounds K and L alone and against PCP disruption of the PPI.

Figures 4A, 4B:
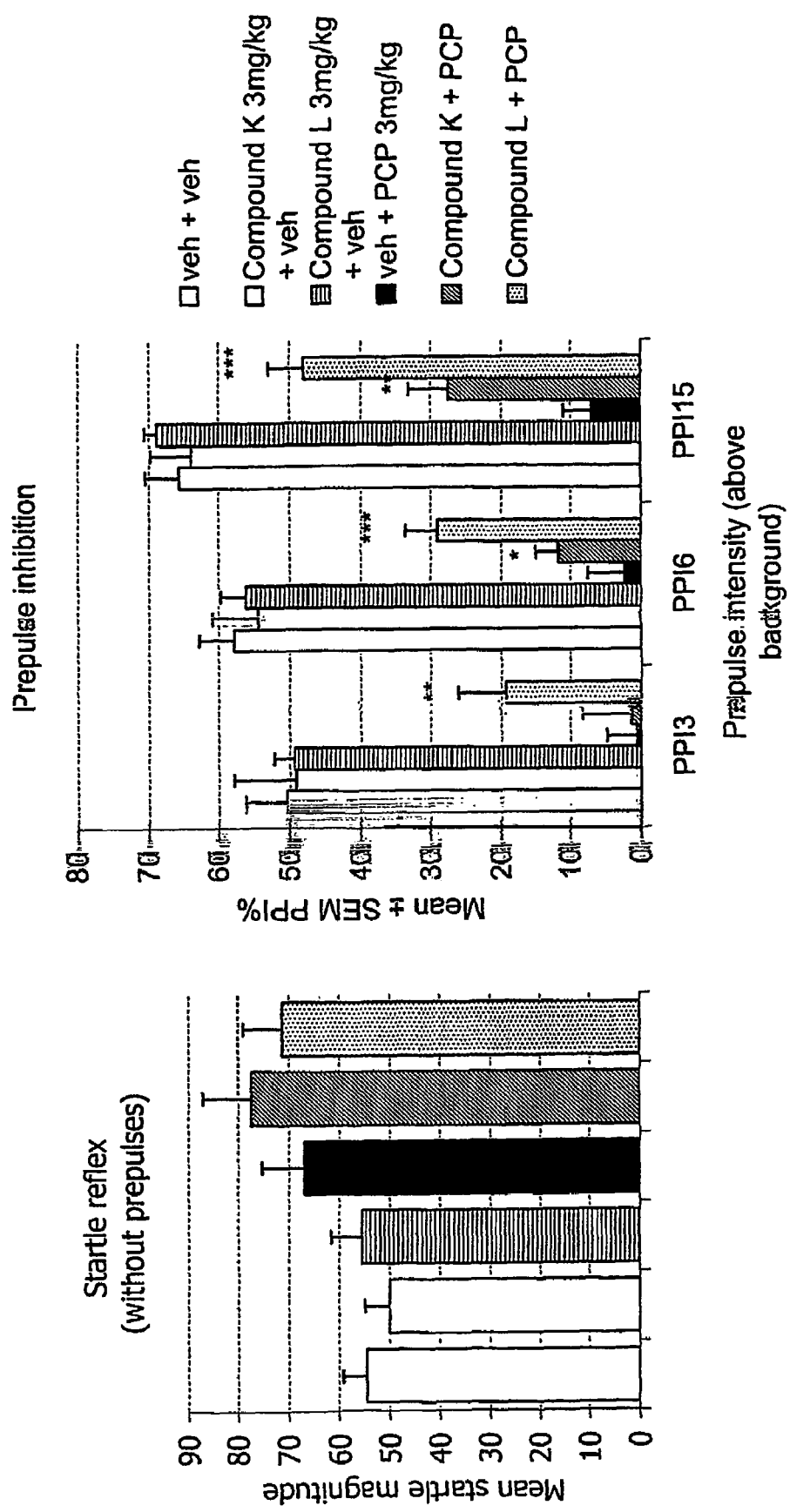
FIGS. 4a and 4b show the effect of compounds K and L on the startle reflex and its prepulse inhibition in rats. (Veh=vehicle). Asterisks as in FIG. 1; comparisons were performed between PCP (phencyclidine)+vehicle and PCP+ compounds K and L.
Figures 5A, 5B:
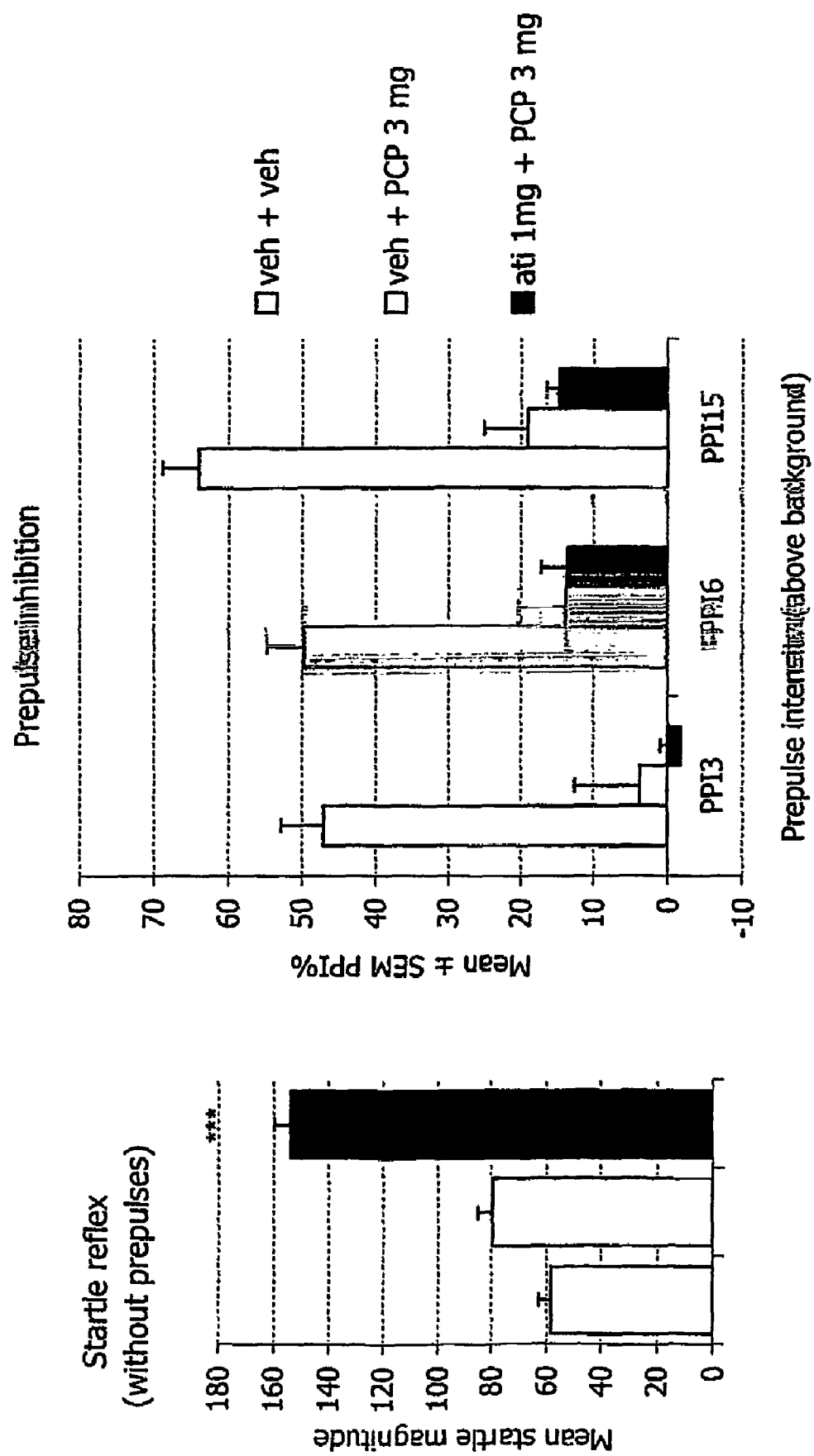
FIGS. 5a and 5b show the effect of the non-selective antagonist atiparnezole (ati) on the startle reflex and its prepulse inhibition in rats in the prescence of phencyclidine (PCP); (veh=vehicle). Asterisks as in FIG. 1, compared to the vehicle+PCP -group.

Groups of rats (n=10/group) were administered the alpha2C-antagonists 20 min before, and PCP or vehicle 10 min before measurement of the acoustic startle reactivity and PPI in a test system designed for startle studies (SR-LAB, San Diego Instrrnents, CA, USA). It was found that the alpha2C-antagonists were able to attenuate the PPI disruption caused by PCP (FIG. 3). This was unexpected and opposite to the hypothesis based on transgenic studies. The non-selective alpha2-antagonist atipamezole produced different effects than was observed with the selective alpha2C-antagonists: atipamezole did not enhance PPI, but it increased the startle reflex per se (i.e. startle without prepulses)(Figure 4).

In conclusion, the results presented in this chapter show that those antagonists which are classified as alpha2C-selective according to in vitro experiments, appeared to fluction as alpha2C-selective antagonists also in vivo in a manner that was predicted based on the available knowledge on alpha2C-antagonism. However, the finding that the alpha2C-antagonists did not decrease PPI, as predicted, but on the contrary, increased PPI, could be considered unexpected and this adds the novelty value of the now proposed usefulness of the compounds of the present invention. The compounds according to the invention may be used to treat any disease or condition wherein alpha-2 antagonists are indicated to be effective. The compounds can also be used to reverse effects induced by alpha-2 agonists. Accordingly, the compounds of the invention may be useful in the treatment of various disorders of the central nervous system (CNS), i.e. different neurological, psychiatric and cognition disorders (such as depression, anxiety disorders, post traumatic stress disorder, schizophrenia, Parkinson's disease and other movement disorders). Furthermore, they may be used in the treatment of various peripheral disorders, e.g. diabetes, orthostatic hypotension, lipolytic disorders (such as obesity), Raynaud's disease or both male and female sexual dysfunctions.

The selective alpha-2C antagonists of the present invention may be used for the treatment of various disorders or conditions of CNS-system where alpha-2C antagonists are indicated to be beneficial, for example, to alleviate the symptoms of various mental disorders propagated by stress, Parkinson's disease, depression, negative symptoms of schizophrenia, attention deficit hyperactivity disorder, post-traumatic stress-disorder, and anxiety disorders.

In addition, due to the novel and previously unpublished findings of the effects of the present alpha2C-antagonists on the PCP—disrupted PPI, the alpha2C-selective compounds can also be used to treat disorders and conditions associated with sensorimotor gating deficits, particularly disorders and conditions wherein the sensorimotor gating deficits results in sensory flooding and cognitive fragmentation causing dysfiunction in attention and perception. Such disorders and conditions include, but are not limited to, schizophrenia, obsessive compulsive disorder, Tourette's syndrome, blepharospasm and other focal dystonias, temporal lobe epilepsy with psychosis, drug-induced psychosis (for example, psychosis caused by chronic use of dopaminergic agents) (Braff, D.L. et al., *Psychopharmacology* (*Berl*) 156(2-3) (2001) 234-258), Huntington's disease, Parkinson's disease, disorders caused by fluctuation of the levels of sex hormones (such as premenstrual syndrome), and panic disorder.

Further, the symptoms which are usually associated with above-mentioned disorders or conditions include, but are not limited to, hallucination, delusion, parathymia, agitation, psychotic cognitive impairment (including deficits in thinking and speech), social withdrawal and withdrawal symptoms (including delirium) associated with cessation of cigarette smoking or alcohol or drug abuse. These symptoms may also be seen in animals in exceptional circumstances, for example, during withdrawal from masters or during transportation.

Due to their selectivity of action, the alpha-2C antagonists of the invention have less or no undesirable side-effects attributed to non-selective alpha2-antagonism, such as increases in blood pressure, heart rate, salival secretions, gastrointestinal secretion, anxiety, and startle reactivity per se (Ruffolo, R. R. J. et al., *Annu Rev Pharmacol Toxicol* 32 (1993) 243-279).

The compound of the invention can be administered for example enterally, topically or parenterally by means of any pharmaceutical formulation useful for said administration, and containing at least one active compound of formula I in pharmaceutically acceptable and effective amounts together with pharmaceutically acceptable diluents, carriers, and/or excipients known in the art. The manufacture of such pharmaceutical formulations is well known in the art.

The therapeutic dose to be given to a patient in need of treatment will vary depending on the compound being administered, the species, age and the sex of the subject being treated, the particular condition being treated, as well as the route and method of administration, and are easily determined by person skilled in the art. Accordingly, the typical dosage for oral administration is from 5 µg/kg to 100 mg/kg per day and that for parenteral administration from 0.5 µg/kg to 10 mglkg for an adult mammal.

The present invention further provides a compound of the invention or an ester or salt thereof for use as alpha-2 antagonist. Furthermore, a method for the treatment of diseases or conditions where alpha-2 antagonists, e.g. alpha-2C antagonists, are indicated to be useful, e.g. a method for the treatment of diseases or conditions of the central nervous system, is provided. In such a method a therapeutically effective amount of a compound of the invention is administered to a subject in need of such treatment. The use of the compounds of the invention for the manufacture of a medicament to be used for the above indications is also provided.

Those skilled in the art will appreciate that the embodiments described in this application could be modified without departing from the broad inventive concept. Those skilled in the art also understand that the invention is not limited to the particular disclosed embodiments, but is intended to also cover modifications to the embodiments that are within the spirit and scope of the invention.

The invention claimed is:

1. A compound of formula IA:

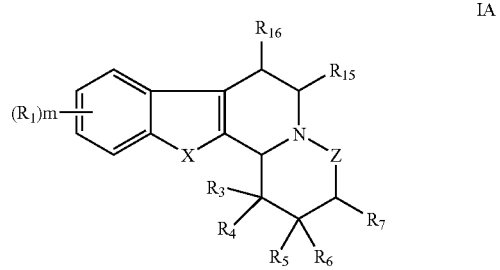

wherein,

X is O or S;

Z is —CHR$_8$—;

R$_1$ is chosen from hydroxy, (C$_1$-C$_6$)alkyl, (C$_1$-C$_6$)alkoxy, halogen, halo(C$_1$-C$_6$)alkyl, (C$_1$-C$_6$)alkoxy-CO—, CN, NO$_2$, NH$_2$, mono- or di(C$_1$-C$_6$)alkylamino, and carboxyl;

R$_3$ is chosen from hydroxy, (C$_1$-C$_6$)alkyl, (C$_2$-C$_6$)alkenyl, hydroxy(C$_1$-C$_6$)alkyl, (C$_1$-C$_6$)alkoxy, (C$_1$-C$_6$)alkoxy (C$_1$-C$_6$)alkyl, hydroxy(C$_1$-C$_6$)alkoxy(C$_1$-C$_6$)alkyl, (C$_3$-C$_7$)cycloalkyl, (C$_3$-C$_4$cycloalkyl(C$_1$-C$_6$)alkyl, aryl, aryl (C$_1$-C$_6$)alkyl, aryloxy, aryl(C$_1$-C$_6$)alkoxy, aryloxy(C$_1$-C$_6$)alkyl, aryl(C$_1$-C$_6$)alkoxy(C$_1$-C$_6$)alkyl, halo(C$_1$-C$_6$) alkyl, NH$_2$, amino(C$_1$-C$_6$)alkyl, mono- or di(C$_1$-C$_6$) alkylamino, mono- or di(C$_1$-C$_6$)alkylamino(C$_1$-C$_6$) alkyl, (C$_1$-C$_6$)alkyl-CO—, (C$_1$-C$_6$)alkyl-CO—O—, (C$_1$-C$_6$)alkyl-CO—O—(C$_1$-C$_6$)alkyl, (C$_1$-C$_6$)alkoxy-CO—, (C$_1$-C$_6$)alkoxy-CO—(C$_1$-C$_6$)alkyl, (C$_1$-C$_6$) alkoxy-CO—(C$_1$-C$_6$)alkoxy(C$_1$-C$_6$)alkyl, carbamoyl, mono- or di(C$_1$-C$_6$)alkylcarbamoyl, carboxyl and (C$_1$-C$_6$)alkyl-S—(C$_1$-C$_6$) alkyl, wherein the (C$_3$-C$_7$)cycloalkyl or aryl group is unsubstituted or is substituted with 1 or 2 substituents each independently chosen from hydroxy, (C$_1$-C$_6$)alkyl, halogen, (C$_1$-C$_6$) alkoxy, NH$_2$, CN and NO$_2$, or one of R$_3$ or R$_4$ and R$_6$ together form a bond between the ring atoms to which they are attached;

R$_4$ is chosen from hydroxy, (C$_1$-C$_6$)alkyl, hydroxy(C$_1$-C$_6$) alkyl, (C$_1$-C$_6$)alkoxy and (C$_1$-C$_6$)alkoxy(C$_1$-C$_6$)alkyl;

R$_5$ is chosen from H, hydroxy, (C$_1$-C$_6$)alkyl, (C$_2$-C$_6$)alkenyl, (C$_1$-C$_6$)alkoxy, (C$_1$-C$_6$)alkoxy(C$_1$-C$_6$)alkyl, (C$_3$-C$_7$)cycloalkyl, (C$_3$-C$_7$)cycloalkyl(C$_1$-C$_6$)alkyl, aryl, aryl(C$_1$-C$_6$)alkyl, aryloxy, aryl(C$_1$-C$_6$)alkoxy, aryloxy (C$_1$-C$_6$)alkyl, aryl(C$_1$-C$_6$)alkoxy(C$_1$-C$_6$)alkyl, halo(C$_1$-C$_6$)alkyl, (C$_1$-C$_6$)alkyl-CO—O—, (C$_1$-C$_6$)alkyl-CO—O—(C$_1$-C$_6$)alkyl, (C$_1$-C$_6$)alkoxy-CO—(C$_1$-C$_6$)alkoxy (C$_1$-C$_6$)alkyl, carbamoyl, mono- or di(C$_1$-C$_6$) alkylcarbamoyl, carboxyl and (C$_1$-C$_6$)alkyl-S—(C$_1$-C$_6$) alkyl, wherein the (C$_3$-C$_7$)cycloalkyl or aryl is unsubstituted or is substituted with 1 or 2 substituents each independently chosen from hydroxy, (C$_1$-C$_6$)alkyl, halogen, (C$_1$-C$_6$) alkoxy, NH$_2$, CN and NO$_2$, or R$_4$ and R$_5$ form, together with the carbon ring atoms to which they are attached, a condensed five to seven membered saturated carbocyclic ring substituted with 1, 2, or 3 substituents, R$_9$, wherein R$_9$ are each independently chosen from hydroxy, (C$_1$-C$_6$)alkyl, halogen, NH$_2$, NO$_2$, (C$_3$-C$_7$)cycloalkyl, hydroxy($C_1$-$C_6$)alkyl, halo($C_1$-$C_6$)alkyl, amino($C_1$-$C_6$)alkyl, mono- or di($C_1$-$C_6$)alkylamino, mono- or di($C_1$-$C_6$)alkylamino($C_1$-$C_6$)alkyl, ($C_1$-$C_6$)alkoxy, ($C_1$-$C_6$)alkoxy($C_1$-$C_6$)alkyl, carboxyl, ($C_1$-$C_6$)alkyl-CO—, ($C_1$-$C_6$)alkyl-CO—O—, ($C_1$-$C_6$)alkoxy-CO—, ($C_1$-$C_6$)alkoxy-CO—($C_1$-$C_6$)alkyl, carbamoyl mono- or di($C_1$-$C_6$)alkylcarbamoyl and oxo;

$R_6$ is chosen from H, hydroxy, ($C_1$-$C_6$)alkyl, ($C_1$-$C_6$)alkoxy and ($C_1$-$C_6$)alkoxy($C_1$-$C_6$)alkyl, or $R_6$ forms a bond between the ring atom to which it is attached and the ring atom to which $R_7$ is attached;

$R_7$ is chosen from H, hydroxy, ($C_1$-$C_6$)alkyl, hydroxy($C_1$-$C_6$)alkyl, ($C_1$-$C_6$)alkoxy and ($C_1$-$C_6$)alkoxy($C_1$-$C_6$)alkyl;

$R_8$ is H, hydroxy, ($C_1$-$C_6$)alkyl, hydroxy($C_1$-$C_6$)alkyl, ($C_1$-$C_6$)alkoxy or ($C_1$-$C_6$)alkoxy($C_1$-$C_6$)alkyl;

$R_{15}$ is chosen from H, ($C_1$-$C_6$)alkyl, ($C_2$-$C_6$)alkenyl, hydroxy($C_1$-$C_6$)alkyl, ($C_1$-$C_6$)alkoxy($C_1$-$C_6$)alkyl, hydroxy($C_1$-$C_6$)alkoxy($C_1$-$C_6$)alkyl, halo($C_1$-$C_6$)alkyl, amino($C_1$-$C_6$)alkyl, mono- or di($C_1$-$C_6$)alkylamino($C_1$-$C_6$)alkyl, ($C_1$-$C_6$)alkyl-CO—, ($C_1$-$C_6$)alkyl-CO—O—($C_1$-$C_6$)alkyl, ($C_1$-$C_6$)alkoxy-CO—, ($C_1$-$C_6$)alkoxy-CO—($C_1$-$C_6$)alkyl, ($C_1$-$C_6$)alkoxy-CO—($C_1$-$C_6$)alkoxy($C_1$-$C_6$)alkyl, carbamoyl, mono- or di($C_1$-$C_6$)alkylcarbamoyl and carboxyl;

$R_{16}$ is chosen from H and ($C_1$-$C_6$)alkyl; and m is 0 to 2;

or a pharmaceutically acceptable salt or ester thereof.

2. The compound according to claim 1, wherein X is O.

3. The compound according to claim 1, wherein X is S.

4. The compound according to claim 1, wherein $R_3$ is chosen from hydroxy, ($C_1$-$C_6$)alkyl, hydroxy($C_1$-$C_6$)alkyl, ($C_1$-$C_6$)alkoxy($C_1$-$C_6$)alkyl, ($C_1$-$C_6$)alkoxy-CO— and ($C_1$-$C_6$)alkyl-CO—O—($C_1$-$C_6$)alkyl, and $R_4$ chosen from is ($C_1$-$C_6$)alkyl and hydroxy($C_1$-$C_6$)alkyl.

5. The compound according to claim 1, wherein $R_3$ is chosen from hydroxy, hydroxy($C_1$-$C_6$)alkyl, and ($C_1$-$C_6$)alkoxy($C_1$-$C_6$)alkyl, and $R_4$ is ($C_1$-$C_6$)alkyl.

6. The compound according to claim 1, wherein $R_4$ and $R_5$ form, together with the carbon ring atoms to which they are attached, a condensed six membered saturated carbocyclic ring.

7. The compound according to claim 1, wherein the compound is 1α-Methyl-1,3,4,5,6,11b-hexahydro-2H-11-oxa-4a-aza-benzo[a]fluoren-1-ol, (1α-Methyl-1,3,4,5,6,11bβ-hexahydro-2H-11-oxa-4a-aza-benzo[a]fluoren-1-yl)-methanol, (−)-(1α-Methyl-1,3,4,5,6,11bβ-hexahydro-2H-11-oxa-4a-aza-benzo[a]fluoren-1-yl)-methanol, (+)-(1α-Methyl-1,3,4,5,6,11bβ-hexahydro-2H-11-oxa-4a-aza-benzo[a]fluoren-1-yl)-methanol, 1α-Isopropyl-1,3,4,5,6,11b-Hexahydro-2H-11-oxa-4a-aza-benzo[a]fluoren-1-ol, 1α-Ethyl-1,3,4,5,6,11bβ-hexahydro-2H-11-oxa-4a-aza-benzo[a]fluoren-1-ol, (1α-Ethyl-1,3,4,5,6,11bβ-hexahydro-2H-11-oxa-4a-aza-benzo[a]fluoren-1-yl)-methanol, (1-Hydroxymethyl-1,3,4,5,6,11b-hexahydro-2H-11-oxa-4a-aza-benzo[a]fluoren-1-yl]-methanol, 1-Methoxymethyl-1α-methyl-1,3,4,5,6,11b β-hexahydro-2H-11-oxa-4a-aza-benzo[a]fluorene, (−)-1-Methoxymethyl-1α-methyl-1,3,4,5,6,11bβ-hexahydro-2H-11-oxa-4a-aza-benzo[a]fluorene, (+)-1-Methoxymethyl-1α-methyl-1,3,4,5,6,11bβ-hexahydro-2H-11-oxa-4a-aza-benzo[a]fluorene, 1α-Methyl-1,3,4,5,6,11b-α-hexahydro-2H-11-oxa-4a-aza-benzo[a]fluorene-1-carboxylic acid ethyl ester, 1-Ethoxymethyl-1α-methyl-1,3,4,5,6,11bβ-hexahydro-2H-11-oxa-4a-aza-benzo [a]fluorene, (1α-Methyl-1,3,4,5,6,11bα-hexahydro-2H-11-oxa-4a-aza-benzo[a]fluoren-1-yl)-methanol, (−)-(1α-Methyl-1,3,4,5,6,11bα-hexahydro-2H-11-oxa-4a-aza-benzo[a]fluoren-1-yl)-methanol, (+)-(1α-Methyl-1,3,4,5,6,11bα-hexahydro-2H-11-oxa-4a-aza-benzo[a]fluoren-1-yl)-methanol, 1α-Ethyl-1,3,4,5,6,11bα-hexahydro-2H-11-oxa-4a-aza-benzo[a]fluorene-1-carboxylic methyl ester, 1-Methoxymethyl-1α-methyl-1,3,4,5,6,11bα-hexahydro-2H-11-oxa-4a-aza-benzo[a]fluorene, (−)-1-Methoxymethyl-1α-methyl-1,3,4,5,6,11bα-hexahydro-2H-11-oxa-4a-aza-benzo[a]fluorene, (+)-1-Methoxymethyl-1α-methyl-1,3,4,5,6,11bα-hexahydro-2H-11-oxa-4a-aza-benzo[a]fluorene, (1α-Ethyl-1,3,4,5,6,11bα-hexahydro-2H-11-oxa-4a-aza-benzo[a]fluoren-1-yl)-methanol or acetic acid 1α-Methyl-1,3,4,5,6,11bβ-hexahydro-2H-11-oxa-4a-aza-benzo[a]fluoren-1-ylmethyl ester.

8. The pharmaceutical composition comprising at least one compound according to claim 1 and a pharmaceutically acceptable diluent, carrier and/or excipient.

* * * * *

UNITED STATES PATENT AND TRADEMARK OFFICE
CERTIFICATE OF CORRECTION

PATENT NO. : 7,592,350 B2
APPLICATION NO. : 10/510019
DATED : September 22, 2009
INVENTOR(S) : David Din Belle et al.

It is certified that error appears in the above-identified patent and that said Letters Patent is hereby corrected as shown below:

In claim 1, column 40, line 30, "$(C_3-C_4 cycloalkyl(C_1-C_6)alkyl,$" should read --$(C_3-C_7)cycloalkyl(C_1-C_6)alkyl,$--.

In claim 4, column 41, line 34, "chosen from is" should read --is chosen from--.

Signed and Sealed this

Tenth Day of November, 2009

David J. Kappos
*Director of the United States Patent and Trademark Office*

UNITED STATES PATENT AND TRADEMARK OFFICE
CERTIFICATE OF CORRECTION

PATENT NO. : 7,592,350 B2  Page 1 of 1
APPLICATION NO. : 10/510019
DATED : September 22, 2009
INVENTOR(S) : Din Belle et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1088 days.

Signed and Sealed this

Twenty-first Day of September, 2010

David J. Kappos
*Director of the United States Patent and Trademark Office*